US011114193B2

(12) United States Patent
Neumann

(10) Patent No.: US 11,114,193 B2
(45) Date of Patent: Sep. 7, 2021

(54) METHODS AND SYSTEMS FOR OPTIMIZING DIETARY LEVELS UTILIZING ARTIFICIAL INTELLIGENCE

(71) Applicant: Kenneth Neumann, Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 0 days.

(21) Appl. No.: 16/502,704

(22) Filed: Jul. 3, 2019

(65) Prior Publication Data

US 2021/0074403 A1 Mar. 11, 2021

(51) Int. Cl.
| | | |
|---|---|---|
| *G06F 16/00* | (2019.01) | |
| *G16H 20/60* | (2018.01) | |
| *G09B 19/00* | (2006.01) | |
| *G16H 20/30* | (2018.01) | |
| *G06F 16/30* | (2019.01) | |

(52) U.S. Cl.
CPC ......... *G16H 20/60* (2018.01); *G09B 19/0092* (2013.01); *G16H 20/30* (2018.01)

(58) Field of Classification Search
None
See application file for complete search history.

(56) References Cited

U.S. PATENT DOCUMENTS

| | | | | |
|---|---|---|---|---|
| 7,873,525 | B1* | 1/2011 | Kraus | G06Q 50/22 |
| | | | | 705/2 |
| 8,234,129 | B2* | 7/2012 | Michon | G06Q 40/08 |
| | | | | 705/3 |
| 8,249,946 | B2* | 8/2012 | Froseth | G06Q 10/08 |
| | | | | 416/72 |
| 8,560,334 | B2 | 3/2013 | Laehteenmaeki | |
| 9,070,175 | B2* | 6/2015 | Hurst | G06Q 50/12 |
| 9,105,041 | B2* | 8/2015 | Harman | G06Q 30/0269 |
| 10,127,361 | B2 | 11/2018 | Hyde et al. | |
| 10,311,372 | B1* | 6/2019 | Hotchkies | H04L 67/32 |

(Continued)

OTHER PUBLICATIONS

Maldarelli, Calire; Popular Science, Oct. 25, 2016; A personalized nutrition company will use your DNA to tell you what to eat; https://www.popsci.com/personalized-nutrition-company-will-use-your-dna-to-tell-you-what-to-eat.

(Continued)

*Primary Examiner* — Polina G Peach
(74) *Attorney, Agent, or Firm* — Caldwell Intellectual Property Law, LLC

(57) ABSTRACT

A system for optimizing dietary levels utilizing artificial intelligence. The system includes at least a server designed and configured to receive at least a dietary request from a user device. The at least a server includes an alimentary instruction set generator module designed and configured to generate at least an alimentary instruction set as a function of the at least a dietary request. The at least a server includes a physical performance instruction set generator designed and configured to receive at least a provider datum, receive at least a physical performance datum, select at least a provider and at least a physical performance executor and generate at least a provider instruction set and at least a physical performance instruction set.

20 Claims, 18 Drawing Sheets

(56) References Cited

U.S. PATENT DOCUMENTS

| | | | | |
|---|---|---|---|---|
| 10,600,105 | B1* | 3/2020 | Kumar | G06Q 30/0637 |
| 2002/0004749 | A1* | 1/2002 | Froseth | G06Q 10/101 |
| | | | | 705/16 |
| 2005/0080650 | A1* | 4/2005 | Noel | G06F 19/3475 |
| | | | | 705/2 |
| 2007/0094090 | A1 | 4/2007 | Jenkins | |
| 2008/0133724 | A1* | 6/2008 | Clark | H04L 67/12 |
| | | | | 709/223 |
| 2008/0178749 | A1* | 7/2008 | Stutman | G06Q 50/12 |
| | | | | 99/494 |
| 2008/0228735 | A1* | 9/2008 | Kenedy | G06F 16/9535 |
| 2009/0043795 | A1* | 2/2009 | Kenedy | G16H 50/20 |
| 2010/0241454 | A1* | 9/2010 | Firminger | G06F 19/3481 |
| | | | | 705/3 |
| 2013/0185646 | A1* | 7/2013 | Wiggins | H04L 67/02 |
| | | | | 715/739 |
| 2013/0304488 | A1* | 11/2013 | Girao | G16H 40/20 |
| | | | | 705/2 |
| 2014/0236759 | A1* | 8/2014 | Mirabile | G06Q 30/0633 |
| | | | | 705/26.8 |
| 2014/0249966 | A1* | 9/2014 | Zaragoza | G06Q 30/0635 |
| | | | | 705/26.81 |
| 2015/0186981 | A1* | 7/2015 | Holman | G07F 9/002 |
| | | | | 705/26.9 |
| 2015/0279171 | A1* | 10/2015 | Hyde | G06Q 10/10 |
| | | | | 340/815.4 |
| 2015/0363860 | A1* | 12/2015 | Lantrip | G06Q 30/0631 |
| | | | | 705/5 |
| 2015/0371553 | A1 | 12/2015 | Vento | |
| 2016/0307128 | A1 | 10/2016 | Herman et al. | |
| 2017/0175169 | A1* | 6/2017 | Lee | G01N 33/54373 |
| 2017/0235912 | A1* | 8/2017 | Moturu | G16H 50/50 |
| | | | | 705/2 |
| 2018/0001184 | A1* | 1/2018 | Tran | H04N 5/2257 |
| 2018/0182479 | A1 | 6/2018 | Castellon et al. | |
| 2018/0189636 | A1 | 7/2018 | Chapela et al. | |
| 2018/0204274 | A1 | 7/2018 | Shimokawa et al. | |
| 2018/0240359 | A1* | 8/2018 | Hujsak | G09B 19/0092 |
| 2018/0240542 | A1 | 8/2018 | Grimmer et al. | |
| 2019/0172587 | A1* | 6/2019 | Park | G16H 50/30 |
| 2019/0385126 | A1* | 12/2019 | Morrow | G06Q 40/08 |
| 2020/0334566 | A1* | 10/2020 | Vianu | G16H 15/00 |

OTHER PUBLICATIONS

Polito, Lisa; Dec. 2, 2016; 3 companies expand the possibilities of personalized nutrition; https://www.newhope.com/products-and-trends/3-companies-expand-possibilities-personalized-nutrition.

Jones, Alexandra; Sep. 22, 2018; The Guardian; Blood, spit and swabs: can you trust home medical-testing kits?; https://www.theguardian.com/global/2018/sep/22/home-medical-testing-kits-blood-spit-swabs-trust-diy.

Habit Food Personalized; 2019; https://habit.com/how-it-works/.

Van Ommen, et al.; Nutrition Reviews vol. 75; Systems biology of personalized nutrition; https://watermark.silverchair.com/nux029.pdf?.

* cited by examiner

METHODS AND SYSTEMS FOR OPTIMIZING DIETARY LEVELS UTILIZING ARTIFICIAL INTELLIGENCE

FIELD OF THE INVENTION

The present invention generally relates to the field of artificial intelligence. In particular, the present invention is directed to methods and systems for optimizing dietary levels utilizing artificial intelligence.

BACKGROUND

Historically, individuals seeking to pursue a healthier lifestyle have been inundated with dietary choices and options. Furthermore, deciding what foods to purchase and how to prepare such foods proves to be a challenge.

SUMMARY OF THE DISCLOSURE

A system for optimizing dietary levels utilizing artificial intelligence the system comprises at least a server. The at least a server is designed and configured to receive at least a dietary request from a user client device. The at least a server includes an alimentary instruction set generator module operating on the at least a server, the alimentary instruction set generator module is designed and configured to generate at least an alimentary instruction set as a function of the at least a dietary request. The at least a server includes a physical performance instruction set generator operating on the at least a server, the generator designed and configured to receive at least a provider datum, receive at least a physical performance datum, select at least a provider and at least a physical performance executor and generate at least a provider instruction set and at least a physical performance instruction set as a function of the at least a provider datum and the at least a physical performance datum and the at least an alimentary instruction set.

A method of optimizing dietary levels utilizing artificial intelligence. The method includes receiving by at least a server at least a dietary request from a user client device. The method includes generating at least an alimentary instruction set as a function of the at least a dietary request. The method includes receiving at least a provider datum. The method includes receiving at least a physical performance datum. The method includes selecting at least a provider and at least a physical performance executor. The method includes generating at least a provider instruction set and at least a physical performance instruction set as a function of the at least a provider datum and the at least a physical performance datum and the at least an alimentary instruction set.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for optimizing dietary levels utilizing artificial intelligence. In an embodiment, at least a server receives at least a dietary request. The at least a dietary request is utilized by the at least a server to generate an alimentary instruction set. In an embodiment, the at least an alimentary instruction set may be generated utilizing training data. The at least a server receives inputs from at least a provider datum and at least a physical performance datum. The at least a server selects a provider and a physical performance executor utilizing a loss function and/or lazy-learning processes. The at least a server generates at least a provider instruction set and at least a physical performance instruction set as a function of the at least a provider datum, the at least a physical performance datum, and the at least an alimentary instruction set.

Figure 1:
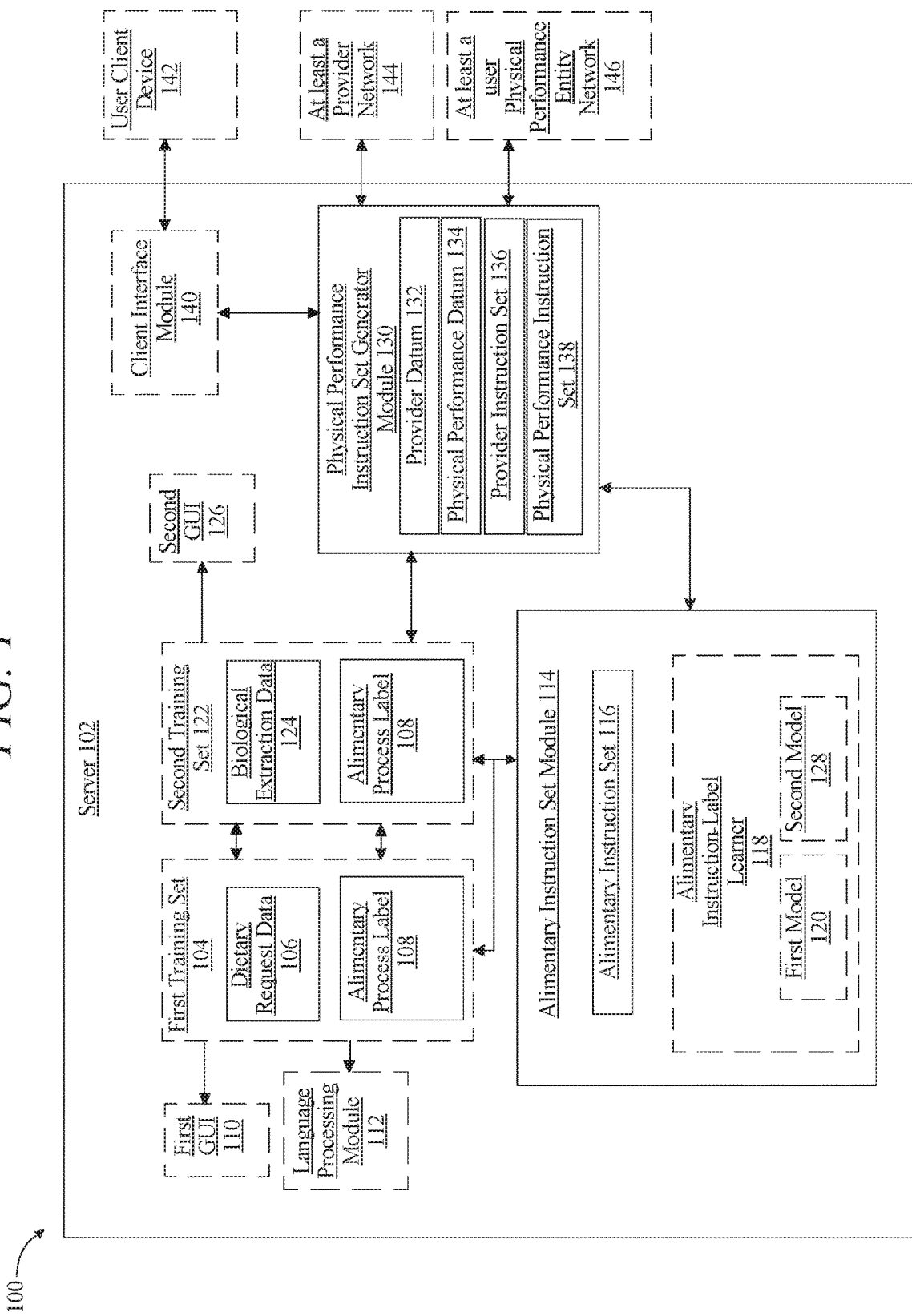
FIG. 1 is a block diagram illustrating an exemplary embodiment of a system for optimizing dietary levels.

Turning now to FIG. 1, a system 100 for optimizing dietary levels utilizing artificial intelligence is illustrated.

System 100 includes at least a server 102. At least a server 102 may include any computing device as described herein, including without limitation a microcontroller, microprocessor, digital signal processor (DSP) and/or system on a chip (SoC) as described herein. At least a server 102 may be housed with, may be incorporated in, or may incorporate one or more sensors of at least a sensor. Computing device may include, be included in, and/or communicate with a mobile device such as a mobile telephone or smartphone. At least a server 102 may include a single computing device operating independently, or may include two or more computing device operating in concert, in parallel, sequentially or the like; two or more computing devices may be included together in a single computing device or in two or more computing devices. At least a server 102 with one or more additional devices as described below in further detail via a network interface device. Network interface device may be utilized for connecting a at least a server 102 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 102 may include but is not limited to, for example, a at least a server 102 or cluster of computing devices in a first location and a second computing device or cluster of computing devices in a second location. At least a server 102 may include one or more computing devices dedicated to data storage, security, distribution of traffic for load balancing, and the like. At least a server 102 may distribute one or more computing tasks as described below across a plurality of computing devices of computing device, which may operate in parallel, in series, redundantly, or in any other manner used for distribution of tasks or memory between computing devices. At least a server 102 may be implemented using a "shared nothing" architecture in which data is cached at the worker, in an embodiment, this may enable scalability of system 100 and/or computing device.

With continued reference to FIG. 1, at least a server 102 and/or one or more modules operating thereon may be designed and/or configured to perform any method, method step, or sequence of method steps in any embodiment described in this disclosure, in any order and with any degree of repetition. For instance, at least a server 102 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 102 and/or one or more modules operating thereon may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, server 102 is configured to receive at least a dietary request. At least a dietary request as used in this disclosure includes a request for a particular diet, food, ingredient, food group, nutrition plan, style of eating, lifestyle, and/or nutrition. At least a dietary request may include a request for a particular type of diet such as Atkins, Paleo, Whole 30, gluten free, ketogenic, dairy free, Mediterranean, soy free, and the like. At least a dietary request may include elimination of certain foods or food groups because of a dislike for such foods, an allergy to a food, and/or a sensitivity. For example, at least a dietary request may include a request for an egg free diet based on a user's aversion to eggs. In yet another non-limiting example, at least a dietary request may include a request for a diet free of bell peppers because of a user's previous IgG food sensitivity testing. At least a dietary request may include a request for a diet free of shellfish because of a user's IgE allergic response to shellfish that was diagnosed when a user was a little child. At least a dietary request may include a request for a diet based on religious or moral beliefs such as kosher diet or vegetarian diet. At least a dietary request may include a request to eliminate certain food groups such as a nightshade free diet or a grain free diet. At least a dietary request may include a request to eliminate certain ingredients that may be commonly found in food such as a request for a diet free of monosodium glutamate (MSG) or corn starch. At least a dietary request may include a request for a certain level or quality of ingredients such as locally sourced ingredients, free range meats, wild caught fish, organic produce and the like. At least a dietary request may include a request for a certain diet because of a previously diagnosed medical condition, such as a user who has been previously diagnosed with *Candida* and is following a low sugar diet. At least a dietary request may include a dietary request based on a certain style of eating that a user prefers, such as low carb, high protein, low fat, and the like. At least a dietary request may include a dietary request as a function of a medication, supplementation, and/or medical treatment or therapy that a user may be undergoing. For example, a user currently taking a medication such as metronidazole may generate at least a dietary request for an alcoholic free diet, while a user currently supplementing with zinc may generate at least a dietary request free of oysters. At least a dietary request may include at least a request for one meal, a specific number of meals such as three meals, or a certain number of meals over a predetermined time period such as a week's worth of meals. At least a dietary request may include a request for specific types of meals such as three breakfasts, two lunches, and one dinner. Meal types and meal numbers ordered may be customized based on user inputs and user reported eating habits. For example, a user who habitually does not eat breakfast may not request breakfast meals, while a user who habitually eats breakfast at home may request a dietary request for only lunch and dinner meals.

With continued reference to FIG. 1, the at least a dietary request may include at least an element of user data including a constitutional restriction. Element of user data as used herein, is any element of data describing the user, user needs, and/or user preference. At least an element of user data may include a constitutional restriction. At least a constitutional restriction may include any constitutional reason that a user may be unable to engage in an alimentary instruction set process; at least a constitutional restriction may include a contraindication such as an injury, a previous diagnosis such as by an informed advisor including a functional medicine doctor, an allergy or food sensitivity issue, a contraindication due to a medication or supplement that a user may be taking. For example, a user diagnosed with a hypercholesteremia and currently taking a cholesterol lowering medication such as a statin may report a constitutional restriction that includes an inability to consume grapefruit containing foods and food products. In yet another non-limiting example, a user diagnosed with a shellfish allergy during childhood may report a constitutional restriction that includes an inability to consume shellfish or any shellfish containing foods and food products. At least an element of user data may include at least a user preference. At least a user preference may include for example religious preferences such as forbidden foods, medical interventions, exercise routines and the like. For example, a user who is of Catholic faith may report a religious preference to not consume animal products on Fridays during lent. At least a user preference may include a user's dislike such as for example a user aversion to certain foods or nutrient groups, such as for example an aversion to eggs or an aversion to beets. At least a user preference may include for example a user's likes such as a user's preference to consume animal products or full fat dairy and the like.

Continuing to refer to FIG. 1, server 102 may designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, server 102 may be configured to receive a first training set 104 including a plurality of data entries, each data entry of the first training set 104 including at least a dietary request data 106 and at least a correlated alimentary process label 108. An "alimentary process label 108," as used in this disclosure, is an element of data identifying a solution and/or suggestion as to nourishment requirements and/or options contained within a dietary request. Alimentary process label 108 may include nourishment requirements and/or options including potential foods, meals, ingredients, and/or supplements that may be compatible for a user to consume as a function of user's dietary request. For example, a dietary request for a gluten free diet may contain an alimentary process label 108 that contains nourishment options such as gluten free toast, gluten free grains such as buckwheat, rice, and amaranth. In yet another non-limiting example, a dietary request for a raw foods diet may contain an alimentary process label 108 that contains nourishment options including fruits such as strawberries, kiwis, and bananas. At least a dietary request data 106 may include any data describing the user, user needs, user dietary preferences, and/or user preferences. Dietary request data 106 may include a constitutional restriction such as an injury, a previous diagnosis from a medical professional such as a functional medicine doctor, an allergy or food sensitivity issue, a contraindication to a medication or supplement and the like. For example, a user diagnosed with colitis and currently taking an antibiotic medication such as metronidazole may report a constitutional restriction that includes restrictions on alcohol consumption. At a least a dietary request data 106 may include religious preferences such as forbidden foods, medical interventions, exercise routines and the like. At least a dietary request data 106 may include a user's dislike such as for example a user aversion to certain foods or nutrient groups, such as for example an aversion to liver or onions. At least a dietary request data 106 may include for example a user's likes such as a user's preference to consume animal protein or plant protein. At least a dietary request data 106 may include for example, a preferred dietary style of eating such as vegetarian, vegan, pescatarian, flexitarian, and the like. At least a dietary request data 106 may include a preferred style of eating such as for example, paleo, ketogenic, gluten free, grain free, low FODMAP, raw food diet, fruitarian, lacto vegetarianism, ovo vegetarianism, intermittent fasting, Mediterranean diet, carb-conscious, gluten free, nightshade free, dairy free, and the like.

With continued reference to FIG. 1, at least an alimentary process label 108 may be correlated with at least a dietary request data 106. In an embodiment, an element of dietary request data 106 is correlated with at least an alimentary process label 108 where the element of dietary data is located in the same data element and/or portion of data element as the alimentary label; for example, and without limitation, an element of dietary data is correlated with an alimentary label where both element of dietary data and alimentary element are contained within the same first data element of the first training set 104. As a further example, an element of dietary data is correlated with an alimentary element where both share a category label as described in further detail below, where each is within a certain distance of the other within an ordered collection of data in data element, or the like. Still further, an element of dietary data may be correlated with an alimentary label where the element of dietary data and the alimentary label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between dietary data and alimentary labels that may exist in first training set 104 and/or first data element consistently with this disclosure.

In an embodiment, and still referring to FIG. 1, server 102 may be designed and configured to associate at least an element of a dietary request with a category from a list of significant categories of dietary request data 106. Significant categories of dietary request data 106 may include labels and/or descriptors describing types of dietary request data 106 that are identified as being of high relevance in identifying alimentary process labels 108. As a non-limiting example, one or more categories may identify significant categories of dietary request data 106 based on degree of relevance to one or more impactful conditions and/or serious adverse events associated with dietary request data. For instance, and without limitation, a particular set of dietary request data 106 that includes anaphylaxis to shellfish may be recognized as utmost importance for a user to avoid all shellfish containing foods even those foods that may contain hidden ingredients containing shellfish derivatives such as oyster sauce as compared to dietary request data 106 that includes a dislike of Brussel sprouts, whereby ingestion of Brussel sprouts may not produce an anaphylactic reaction but rather is more indicative of a dislike. As a non-limiting example, and without limitation, dietary request data 106 describing gluten avoidance such as a gluten intolerance, Celiac Disease, wheat allergy, atopic dermatitis, fructose malabsorption, non-Celiac gluten sensitivity, dermatitis herpetiformis, IgE mediated gluten allergy, IgG mediated gluten sensitivity may be recognized as useful for identifying avoidance of various gluten containing foods and ingredients such as wheat, barley, oats, malt, croutons, corn flakes, couscous, pancakes, beer, brewer's yeast, and flour tortillas. In a further non-limiting example, dietary request data 106 describing gluten avoidance may be useful for identifying certain categories of foods such as grains, alcoholic beverages, sauces, dressings, baked goods, starches, and the like. Persons skilled in the art, upon reviewing the entirety of this disclosure, will be aware of various additional categories of physiological data that may be used consistently with this disclosure.

Still referring to FIG. 1, server 102 may receive the list of significant categories according to any suitable process; for instance, and without limitation, server 102 may receive the list of significant categories from at least an expert. In an embodiment, server 102 and/or a user device connected to server 102 may provide a first graphical user interface 110, which may include without limitation a form or other graphical element having data entry fields, wherein one or more experts, including without limitation clinical and/or scientific experts, may enter information describing one or more categories of dietary data that the experts consider to be significant or useful for detection of conditions; fields in graphical user interface may provide options describing previously identified categories, which may include a comprehensive or near-comprehensive list of types of dietary data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to alimentary labels, where experts may enter data describing alimentary labels and/or categories of alimentary labels the experts consider related to entered categories of dietary request data; for instance, such fields may include drop-down lists or other pre-populated data entry fields listing currently recorded alimentary labels, and which may be comprehensive, permitting each expert to select an alimentary label and/or a plurality of alimentary labels the expert believes to be predicted and/or associated with each category of dietary request data selected by the expert. Fields for entry of alimentary labels and/or categories of alimentary labels may include free-form data entry fields such as text entry fields; as described above, examiners may enter data not presented in pre-populated data fields in the free-form data entry fields. Alternatively or additionally, fields for entry of alimentary labels may enable an expert to select and/or enter information describing or linked to a category of alimentary label that the expert considers significant, where significance may indicate likely impact on longevity, mortality, quality of life, or the like as described in further detail below. First graphical user interface 110 may provide an expert with a field in which to indicate a reference to a document describing significant categories of dietary data, relationships of such categories to alimentary labels, and/or significant categories of alimentary labels. Any data described above may alternatively or additionally be received from experts similarly organized in paper form, which may be captured and entered into data in a similar way, or in a textual form such as a portable document file (PDF) with examiner entries, or the like With continued reference to FIG. 1, data information describing significant categories of dietary request data, relationships of such categories to alimentary labels, and/or significant categories of alimentary labels may alternatively or additionally be extracted from one or more documents using a language processing module 112. Language processing module 112 may include any hardware and/or software module. Language processing module 112 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 112 may compare extracted words to categories of dietary request data, one or more alimentary process labels 108, and/or one or more categories of alimentary process labels 108 recorded at server 102; such data for comparison may be entered on server 102 as described above using expert data inputs or the like. In an embodiment, one or more categories may be enumerated, to find total count of mentions in such documents. Alternatively or additionally, language processing module 112 may operate to produce a language processing model. Language processing model may include a program automatically generated by server 102 and/or language processing module 112 to produce associations between one or more words extracted from at least a document and detect associations, including without limitation mathematical associations, between such words, and/or associations of extracted words with categories of dietary data, relationships of such categories to alimentary labels, and/or categories of alimentary labels. Associations between language elements, where language elements include for purposes herein extracted words, categories of dietary data, relationships of such categories to alimentary labels, and/or categories of alimentary labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of dietary request data, a given relationship of such categories to alimentary process labels 108, and/or a given category of alimentary process labels 108. As a further example, statistical correlations and/or mathematical associations may include probabilistic formulas or relationships indicating a positive and/or negative association between at least an extracted word and/or a given category of dietary request, a given relationship of such categories to alimentary process labels 108, and/or a given category of alimentary process labels 108; positive or negative indication may include an indication that a given document is or is not indicating a category of dietary request data, relationship of such category to alimentary process label 108, and/or category of alimentary labels is or is not significant. For instance, and without limitation, a negative indication may be determined from a phrase such as "whole wheat bread was not found to be compatible with a gluten free diet," whereas a positive indication may be determined from a phrase such as "coconut milk was found to be compatible with a lactose free diet" as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at server 102, or the like.

Still referring to FIG. 1, language processing module 112 and/or server 102 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of dietary data, a given relationship of such categories to alimentary labels, and/or a given category of alimentary labels. There may be a finite number of category of dietary data, a given relationship of such categories to alimentary labels, and/or a given category of alimentary labels to which an extracted word may pertain; an HMM inference algorithm, such as the forward-backward algorithm or the Viterbi algorithm, may be used to estimate the most likely discrete state given a word or sequence of words. Language processing module 112 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 112 may use a corpus of documents to generate associations between language elements in a language processing module 112, and server 102 may then use such associations to analyze words extracted from one or more documents and determine that the one or more documents indicate significance of a category of dietary data, a given relationship of such categories to labels, and/or a given category of alimentary labels. In an embodiment, server 102 may perform this analysis using a selected set of significant documents, such as documents identified by one or more experts as representing good science, good clinical analysis, or the like; experts may identify or enter such documents via graphical user interface as described below in reference to FIG. 4, or may communicate identities of significant documents according to any other suitable method of electronic communication, or by providing such identity to other persons who may enter such identifications into server 102. Documents may be entered into server 102 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, server 102 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of dietary data, a given relationship of such categories to alimentary labels, and/or a given category of alimentary labels is entered via graphical user interface, alternative submission means, and/or extracted from a document or body of documents as described above, an entry or entries may be aggregated to indicate an overall degree of significance. For instance, each category of dietary data, relationship of such categories to alimentary labels, and/or category of alimentary labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of dietary data, relationships of such categories to alimentary labels, and/or categories of alimentary labels may be ranked according significance scores, for instance by ranking categories of dietary data, relationships of such categories to alimentary labels, and/or categories of alimentary labels higher according to higher significance scores and lower according to lower significance scores. Categories of dietary data, relationships of such categories to alimentary labels, and/or categories of alimentary labels may be eliminated from current use if they fail a threshold comparison, which may include a comparison of significance score to a threshold number, a requirement that significance score belong to a given portion of ranking such as a threshold percentile, quartile, or number of top-ranked scores.

Still referring to FIG. 1, server 102 may detect further significant categories of dietary data, relationships of such categories to alimentary labels, and/or categories of alimentary labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, server 102 may be configured, for instance as part of receiving the first training set 104, to associate at least correlated first alimentary label 110 with at least a category from a list of significant categories of alimentary labels. Significant categories of alimentary labels may be acquired, determined, and/or ranked as described above. As a non-limiting example, alimentary labels may be organized according to relevance to and/or association with a list of significant foods or food groups. A list of significant foods or food groups may include, without limitation, foods having generally acknowledged impact on dietary request. For example, a dietary request such as a grain free diet may be associated with a list of significant foods such as actual grains, grain containing condiments such as ketchup that contains starch thickening agents, grain containing breakfast foods such as pastries and cereals, grain containing frozen foods, grain containing meats and the like.

With continued reference to FIG. 1, system 100 includes an alimentary instruction set generator module 114 operating on the at least a server. The alimentary instruction set generator module 114 may include any hardware and/or software module as described in this disclosure. Alimentary instruction set generator module 114 is designed and configured to generate at least an alimentary instruction set as a function of the at least a dietary request and the training data. In an embodiment, alimentary instruction set 116 is a data structure containing a solution and/or suggestion to nourishment requirements as requested in the at least a dietary request. Alimentary instruction set may contain suggestions as to foods and/or meals that a user may consume that may meet requirements and/or specifications of at least a dietary request. the at least a dietary request and training data. For example, at least a dietary request containing a request for a dairy free diet may be utilized to generate an alimentary instruction set that includes a suggestion for breakfast that includes oatmeal topped with coconut milk. In yet another non-limiting example, at least a dietary request for a vegetarian diet may be utilized to generate an alimentary instruction set that includes a meal containing tofu, spinach, and rice. In an embodiment, alimentary instruction set generator module 114 may be configured to modify alimentary instruction set as a function of the at least a user entry as described in more detail below.

With continued reference to FIG. 1, alimentary instruction set module 114 may include an alimentary instruction label learner 118, the alimentary instruction label learner 118 designed and configured to generate a correlated alimentary process label 108. Alimentary instruction label learner 118 may include any hardware and/or software module. Alimentary instruction label learner 118 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 1, alimentary instruction label learner 118 may be designed and configured to generate at least an alimentary instruction set by creating at least a first machine-learning model 120 relating dietary request data 106 to alimentary labels using the first training set 104 and generating the at least an alimentary instruction set using the first machine-learning model 120; at least a first machine-learning model 120 may include one or more models that determine a mathematical relationship between dietary request data 106 and alimentary labels. An "alimentary instruction set" as used in this disclosure is a data structure containing a solution and/or suggestion as to nourishment requirements and/or preferences contained within at least a dietary request. Alimentary instruction set may include meals, foods, food groups, ingredients, supplements and the like that may be compatible with at least a dietary request. For example, alimentary instruction set may include a list of three possible meals that may be compatible with at least a dietary request for a dairy free diet. In yet another non-limiting example, alimentary instruction set may include food groups compatible with at least a dietary request such as a dietary request for a paleo diet may include recommendations as to food groups that are compatible including meats, fish, poultry, fats, vegetables, and fruits. Machine-learning models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, machine-learning algorithms may generate alimentary instruction sets as a function of a classification of at least an alimentary label. Classification as used herein includes pairing or grouping alimentary labels as a function of a shared commonality. Classification may include for example, groupings, pairings, and/or trends between dietary data and current alimentary label, future alimentary label, and the like. In an embodiment, machine-learning algorithms may examine relationships between a future propensity of a user to require a new alimentary instruction set based on current dietary data. Machine-learning algorithms may include any and all algorithms as performed by any modules, described herein for alimentary instruction label learner 118. For example, machine-learning algorithms may relate a dietary request such as a grain free diet to a user's future propensity to require an alimentary instruction set containing a recommendation to consume high fiber foods. Machine-learning algorithms may examine precursor dietary requests and future propensity to report a subsequent dietary request. For example, machine-learning algorithms may examine a user dietary request for a gluten free diet with a future propensity to report a subsequent dairy free diet. In yet another non-limiting example, machine learning algorithms may examine varying degrees of dietary requests and restrictions. For example, machine-learning algorithms may examine a user dietary request for Atkins diet with a future propensity to report a less restrictive dietary request such as the South Beach Diet. In yet another non-limiting example, machine-learning algorithms may examine a user dietary request for a gluten free diet with a future propensity to report a more restrictive dietary request such as a ketogenic diet. Machine-learning algorithms may examine a user dietary request for vegetarian diet with a future propensity to report a request for a vegan diet. Machine-learning algorithms may examine degree of dietary restriction requests and development of food allergies over time. For example, machine-learning algorithms may examine a user dietary request for an elimination diet with a future propensity to report a less restrictive diet as foods are reintroduced. Machine-learning algorithms may examine dietary requests by categories, such as demographics including geographic location, age, sex, marital status, profession, income, and the like. For example, machine learning algorithms may examine user dietary requests in California versus user dietary requests in Maine. Machine-learning algorithms may examine dietary requests including several categories such as user dietary requests in men between the ages of 45-55 in Alaska versus user dietary requests among females age 18-24 in Alabama. Machine-learning algorithms may examine trends among dietary requests generated such as for example, a dietary request by a user for vegetarian options and subsequent requests by the user for carnivore dietary requests.

Continuing to refer to FIG. 1, machine-learning algorithm used to generate first machine-learning model 120 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, alimentary instruction label learner 118 may generate alimentary instruction set using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 104; the trained network may then be used to apply detected relationships between elements of dietary request data 106 and alimentary labels.

With continued reference to FIG. 1, machine-learning algorithms may include unsupervised processes; unsupervised processes may, as a non-limiting example, be executed by an unsupervised learning module executing on server 102 and/or on another computing device in communication with server 102, which may include any hardware or software module as described as described herein. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, alimentary instruction label learner 118 and/or server 102 may perform an unsupervised machine learning process on first training set 104, which may cluster data of first training set 104 according to detected relationships between elements of the first training set 104, including without limitation correlations of elements of dietary request data 106 to each other and correlations of alimentary labels to each other; such relations may then be combined with supervised machine learning results to add new criteria for alimentary instruction label learner 118 to apply in relating dietary request data 106 to alimentary labels. As a non-limiting, illustrative example, an unsupervised process may determine that a first element of dietary data closely with a second element of dietary data, where the first element has been linked via supervised learning processes to a given alimentary label, but the second has not; for instance, the second element may not have been defined as an input for the supervised learning process, or may pertain to a domain outside of a domain limitation for the supervised learning process. Continuing the example a close correlation between first element of dietary request data 106 and second element of dietary request data 106 may indicate that the second element is also a good predictor for the alimentary label; second element may be included in a new supervised process to derive a relationship or may be used as a synonym or proxy for the first dietary data by alimentary label learner 114.

Still referring to FIG. 1, server 102 and/or alimentary instruction label learner 118 may detect further significant categories of dietary data, relationships of such categories to alimentary labels, and/or categories of alimentary labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, alimentary instruction label learner 118 and/or server 102 may continuously or iteratively perform unsupervised machine-learning processes to detect relationships between different elements of the added and/or overall data. Use of unsupervised learning may greatly enhance the accuracy and detail with which system may detect alimentary labels.

With continued reference to FIG. 1, unsupervised processes may be subjected to domain limitations. For instance, and without limitation, an unsupervised process may be performed regarding a comprehensive set of data regarding one person, such as demographic information including age, sex, race, geographical location, profession, and the like. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of dietary data, a group of people having a shared value for an element and/or category of alimentary label, and/or a group of people having a shared value and/or category of alimentary label; as illustrative examples, cohort could include all people requesting a gluten free diet, all people requesting a dairy free diet, all people requesting a grain free diet, all people requesting a vegetarian diet or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 1, alimentary instruction label learner 118 may alternatively or additionally be designed and configured to generate an alimentary instruction set by executing a lazy learning process as a function of the first training set 104 and the at least a dietary request; lazy learning processes may be performed by a lazy learning module executing on server 102 and/or on another computing device in communication with server 102, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at an alimentary label associated with a dietary request, using first training set 104. As a non-limiting example, an initial heuristic may include a ranking of alimentary labels according to relation to a test type of at least a dietary request, one or more categories of dietary data identified in test type of at least a dietary request, and/or one or more values detected in at least a dietary request; ranking may include, without limitation, ranking according to significance scores of associations between elements dietary data and alimentary labels, for instance as calculated as described above. Heuristic may include selecting some number of highest-ranking associations and/or alimentary labels. Alimentary instruction label learner 118 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate alimentary outputs as described in this disclosure, including without limitation lazy learning applications of machine-learning algorithms as described in further detail below.

Continuing to refer to FIG. 1, alimentary instruction label learner 118 may generate a plurality of alimentary labels having different implications for a particular person. For instance, where the at least a dietary request includes a request for a gluten free diet, alimentary instruction sets may be consistent with recommendations for meals containing grains such as rice, *quinoa*, teff, millet, buckwheat, amaranth, sorghum and the like. In such a situation, alimentary instruction label learner 118 and/or server 102 may perform additional processes to resolve ambiguity. Processes may include presenting multiple possible results to a user, informing the user that one or more dietary preferences are needed to determine a more definite alimentary label, such as a user preference for a gluten free grain of *quinoa* over millet. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, alimentary instruction label learner 118 and/or server 102 may operate a further algorithm to determine which of the multiple outputs is most likely to be correct; algorithm may include use of an additional supervised and/or unsupervised model. Alternatively or additionally, alimentary instruction label learner 118 may perform one or more lazy learning processes using a more comprehensive set of user data to identify a more probably correct result of the multiple results. Results may be presented and/or retained with rankings, for instance to advise a user of the relative probabilities of various alimentary labels being correct; alternatively or additionally, alimentary labels associated with a probability of correctness below a given threshold and/or alimentary labels contradicting results of the additional process, may be eliminated. As a non-limiting example, a dietary request for a vegetarian diet may lead to animal containing meat products such as beef, chicken, and lamb from being eliminated from a list of alimentary labels for a user while alimentary labels containing animal derived dairy products such as yogurt, cheese, and milk may be retained. Similarly, a dietary request for a vegan diet may eliminate all animal derived products but retain all plant sourced products including tofu, soybeans, beans, seitan, tempeh, lentils, and the like. Persons skilled in the art, upon reviewing the entirety of this disclosure, will be aware of various ways in which additional processing may be used to determine relative likelihoods of alimentary labels on a list of multiple alimentary labels, and/or to eliminate some labels from such a list. Alimentary instruction set may be provided to user output device as described in further detail below.

With continued reference to FIG. 1, receiving by the at least a server 102 the at least a dietary request from a user device may include receiving at least a biological extraction from a user. At least a biological extraction may include any element of physiological data. Physiological data may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin Al—C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 204 may include one or more measures of psychological function or state, such as without limitation clinical interviews, assessments of intellectual functioning and/or intelligence quotient (IQ) tests, personality assessments, and/or behavioral assessments. Physiological state data 204 may include one or more psychological self-assessments, which may include any self-administered and/or automatedly computer-administered assessments, whether administered within system 100 and/or via a third-party service or platform.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

With continued reference to FIG. 1, physiological state data may include one or more evaluations of sensory ability, including measures of audition, vision, olfaction, gustation, vestibular function and pain. Physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein, is data describing all proteins produced and/or modified by an organism, colony of organisms, or system of organisms, and/or a subset thereof. Physiological state data may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below. Physiological state data may include any physiological state data, as described above, describing any multicellular organism living in or on a person including any parasitic and/or symbiotic organisms living in or on the persons; non-limiting examples may include mites, nematodes, flatworms, or the like.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Examples of physiological state data described in this disclosure are presented for illustrative purposes only and are not meant to be exhaustive. Persons skilled in the art, upon reviewing the entirety of this disclosure, will be aware of various additional examples of physiological state data that may be used consistently with descriptions of systems and methods as provided in this disclosure.

At least a biological extraction may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, blood sugar, and/or blood pressure. At least a sensor 108 may be configured to detect internal and/or external biomarkers and/or readings. At least a sensor may be a part of system 100 or may be a separate device in communication with system 100.

Still referring to FIG. 1, at least a biological extraction may include any data suitable for use as physiological state data as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 102 may present to user a set of assessment questions designed or intended to evaluate a current state of mind of the user, a current psychological state of the user, a personality trait of the user, or the like; at least a server 102 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, server 102 may be designed and configured to receive a second training set 122 including a plurality of second data entries. Each second data entry of the second training set 122 includes at least an element of biological extraction data 122; at least an element of biological extraction data 122 may include any data describing a biological extraction, including any of the biological extractions and/or physiological data as described above. Each second data entry of the second training set 122 includes at least an alimentary process label 108 correlated with the biological extraction data 122, where correlation may include any correlation suitable for correlation of dietary request data 106 to alimentary process label 108 as described above. Alimentary process label 108 may include any of the alimentary process labels 108 as described above.

With continued reference to FIG. 1, server 102 may be configured, for instance as part of receiving second training set 122, to associate biological extraction data 124 with at least a category from a list of significant categories of biological extraction data. This may be performed as described above for use of lists of significant categories with regard to dietary request data 106. Significance may be determined, and/or associated with at least a category, may be performed for biological extraction data 122 in second training set 122 according to a first process as described above for first training set 104. For example, categories may include Still referring to FIG. 1, server 102 may be configured, for instance as part of receiving second training set 122, to associate at least an alimentary process label 108 with at least a category from a list of significant categories of alimentary process labels 108. In an embodiment, server 102 and/or a user device connected to server may provide a second graphical user interface 126 which may include without limitation a form or other graphical element having data entry fields, wherein one or more experts, including without limitation clinical and/or scientific experts, may enter information describing one or more categories of biological extraction data 124 that the experts consider to be significant as described above; fields in graphical user interface may provide options describing previously identified categories, which may include a comprehensive or near-comprehensive list of types of biological extraction data, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to alimentary process labels 108, where experts may enter data describing alimentary process labels and/or categories of alimentary process labels the experts consider related to entered categories of biological extraction data; for instance, such fields may include drop-down lists or other pre-populated data entry fields listing currently recorded alimentary labels, and which may be comprehensive, permitting each expert to select an alimentary label and/or a plurality of alimentary labels the expert believes to be predicted and/or associated with each category of biological extraction data selected by the expert. Fields for entry of alimentary labels and/or categories of alimentary labels may include free-form data entry fields such as text entry fields; as described above, examiners may enter data not presented in pre-populated data fields in the free-form data entry fields. Alternatively or additionally, fields for entry of alimentary labels may enable an expert to select and/or enter information describing or linked to a category of alimentary label and/or biological extraction data that the expert considers significant, where significance may indicate likely impact on longevity, mortality, quality of life, or the like as described in further detail below. Graphical user interface may provide an expert with a field in which to indicate a reference to a document describing significant categories of biological extraction data, relationships of such categories to alimentary process labels, and/or significant categories of alimentary process labels. Such information may alternatively be entered according to any other suitable means for entry of expert data as described above. Data concerning significant categories of biological extraction data, relationships of such categories to alimentary process labels, and/or significant categories of alimentary process labels may be entered using analysis of documents using language processing module 112 or the like as described above.

With continued reference to FIG. 1, alimentary instruction label learner 118 may be configured to create a second machine-learning model 128 relating biological extraction data 124 to alimentary process labels 108 using the second training set 122 and generate alimentary instruction set 116 using the second machine-learning model 128. Second machine-learning model 128 may be generated according to any process, process steps, or combination of processes and/or process steps suitable for creation of first machine-learning model 120.

With continued reference to FIG. 1, system 100 includes a physical performance instruction set generator module 130 operating on the at least a server. The physical performance instruction set generator module 130 may include any hardware and/or software module as described in this disclosure. Physical performance instruction set generator module 130 is designed and configured to receive at least a provider datum, receive at least a physical performance datum, select at least a provider and select at least a physical performance executor, and generate at least a provider instruction set and at least a physical performance instruction set as a function of the at least a provider datum and the at least a physical performance datum and the at least an alimentary instruction set.

With continued reference to FIG. 1, physical performance instruction set generator module 130 receives at least a provider datum 132. At least a provider datum 132 as used herein, is any element of data describing the provider, the provider's ability to prepare food for a certain dietary request, the provider's preference to prepare food within a certain geographical location, and/or a menu selection of food options that a provider may be able to prepare such as a weekly menu of food options. Provider as used herein, includes any participant involved in preparation of at least a dietary request. Provider may include a restaurant such as a local privately owned restaurant or a chain restaurant that is located at multiple locations. Provider may include a company that prepares pre-packaged meals. Provider may include a grocery store that prepares meals and may include a restaurant located within the grocery store. Provider may include a chef or cook who prepares meals at home or in a private commercialized kitchen. Provider may include a chef or cook who prepares meals in a school or kitchen or space that the chef or cook rents out for example. Providers may execute a provider performance. A provider performance may include any action involved in the preparation of and/or pursuant to at least a dietary request. A provider performance may include preparation of a meal that adheres to a dietary request from a user such as preparing a gluten free lunch for a user. A provider performance may include preparation of a week's worth of meals for a user with a dietary request for the ketogenic diet. Provider datum 132 may include for example, data describing a menu option for three meals a provider may be able to prepare for a user with a gluten intolerance for dinner. Provider datum 132 may include for example, data describing menu options that are free of certain allergens such as eggs, shellfish, gluten, dairy, and the like. Provider datum 132 may include for example, a time range of how long it may take a provider to prepare a dietary request or what hours provider is available to prepare a dietary request. Provider datum 132 may include standards of certain ingredients that a provider may prepare foods and meals with, such as locally sourced ingredients, free-range poultry, grass-fed meats, organic ingredients, natural ingredients, and the like.

With continued reference to FIG. 1, physical performance instruction set generator module 130 receives at least a physical performance datum 134. At least a physical performance datum 134, as used herein, is any element of data describing the physical performance executor, the physical performance executor's ability to deliver a dietary request such as a meal based on certain constraints such as a physical performance executor's ability to deliver a dietary request such as a meal within a certain amount of time, the physical performance executor's ability to pick up a dietary request such as a meal from a provider within a certain geographical location, the physical performance executor's ability to deliver a dietary request such as a meal to a user located within a certain geographical location or the like. Physical performance executor as used herein includes any transportation channel that executes the physical performance instruction set. Physical performance executor may include an individual operator of a mode of transportation to deliver a dietary request such as an automobile, bicycle, scooter, boat, bus, airplane, drone, helicopter, train, and the like. Physical performance executor may execute a physical performance. Physical performance includes any action that is directed at delivering at least a dietary request. Physical performance executor may include an individual who works for a ride sharing company such as a taxicab service or a peer to peer ridesharing service. Physical performance executor may include a common carrier such as air common carriers and ground common carriers. Physical performance executor may include any grocery delivery service. Physical performance executor may include any food delivery service. Executing the physical performance instruction may include for example, picking up dietary request such as a meal from a provider and delivering the dietary request to a user. Physical performance instruction set may include any of the physical performance instruction sets as described in more detail below. In an embodiment, physical performance executor may execute a performance by picking up a user dietary request from a provider and delivering the dietary request to the user. In an embodiment, physical performance may be segmented whereby a first physical performance executor may pick up a user dietary request from a provider and deliver the dietary request to a second physical performance executor who may deliver the user dietary request to the user.

With continued reference to FIG. 1, physical performance instruction set generator module 130 may select at least a provider and at least a physical performance executor by generating a loss function of user specific variables and minimizing the loss function. In an embodiment, physical performance instruction set generator module 130 may compare one or more provider options and one or more physical performance executor options to a mathematical expression representing an optimal combination of user entered variables. Mathematical expression may include a linear combination of variables, weighted by coefficients representing relative importance of each variable in generating an optimal provider instruction set and an optimal physical performance instruction set. For instance, a variable such as total time to delivery may be multiplied by a first coefficient representing the importance of total time to delivery, a second variable such as provider menu options may be multiplied by a second coefficient representing the importance of provider menu options, a degree of variance from a delivery instruction set and/or provider instruction set may be represented as another parameter, which may be multiplied by an additional coefficient representing an importance of that variable; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

With continued reference to FIG. 1, mathematical expression may represent a loss function, where a "loss function" is an expression of an output of which an optimization algorithm minimizes to generate an optimal result. As a non-limiting example, physical performance instruction set generator module 130 may calculate variables of each of a plurality of provider instruction sets and physical performance instruction sets, calculate an output of mathematical expression using the variables, and select a provider instruction set and physical performance instruction set that produces an output having the lowest size, according to a given definition of "size" of the set of outputs representing each of the plurality of provider instruction set and physical performance instruction sets; size may, for instance, include absolute value, numerical size, or the like. Selection of different loss functions may result in identification of different provider instruction sets and physical performance instruction sets as generating minimal outputs; for instance, where total time to delivery is associated in a first loss function with a large coefficient or weight, a total time to delivery having a shorter time to delivery may minimize the first loss function, whereas a second loss function wherein total time to delivery has a smaller coefficient but degree of variance from provider menu options has a larger coefficient may produce a minimal output for a different provider instruction set and having a longer total time to delivery but more closely hewing to a provider menu option.

Alternatively or additionally, and still referring to FIG. 1, each provider instruction set and each physical performance instruction set may be represented by a mathematical expression having the same form as mathematical expression; physical performance instruction set generator module 130 may compare the former to the latter using an error function representing average difference between the two mathematical expressions. Error function may, as a non-limiting example, be calculated using the average difference between coefficients corresponding to each variable. Provider instruction set and physical performance instruction set having a mathematical expression minimizing the error function may be selected, as representing an optimal expression of relative importance of variables to a system or user. In an embodiment, error function and loss function calculations may be combined; for instance, a variable resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to variables. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each variable to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of dietary requests, biological extractions, and/or alimentary process labels.

With continued reference to FIG. 1, selecting at least a provider and at least a physical performance executor may include producing a field of combinations of the at least a provider and the at least a physical performance executor and selecting the at least a provider and the at least a physical performance executor using a lazy-learning process. Lazy-learning process may include any of the lazy-learning process as described above. Lazy-learning process may include for example, k-nearest neighbors algorithm, a lazy naïve Bayes algorithm, or the like; persons skilled in the art, upon reviewing the entirety of this disclosure, will be aware of various lazy-learning algorithms that may be applied. Lazy-learning process may include a continuously updating mathematical expression such as continuously updating training sets with new entries based on one or more user entries. User entries may update mathematical expressions, and subsequently be utilized to generate a new training set to modify the new expression. In an embodiment, lazy-learning process may include performing a k-nearest neighbors algorithm, so as to predict the classification of a new sample point based on already known data or training data. In an embodiment, k-nearest neighbors algorithm may assign a weighted contribution of each neighbor, so that nearer neighbors contribute more to the average than the more distant ones. For example, a weighting scheme may include giving each neighbor a weight of 1/d where d is the distance to the neighbor. The neighbor may include a set of data for which the class is known, such as training data. In an embodiment, k-nearest neighbors algorithm may include using training data such as vectors in a multidimensional space, each containing a class label. The training data initially used to generate the k-nearest neighbors algorithm may include a first training set that includes the vector and correlated class label. In an embodiment, subsequent data may be classified during the classification phase, whereby k is a user-defined constant based on the first training set and a subsequent unlabeled vector is classified by assigning a class label that is most frequent among the k training samples nearest to that vector space. In an embodiment, vector space may be measured using Euclidean distance. In an embodiment, classification accuracy calculations based on k values may be updated using algorithms including Large Margin Nearest Neighbor and/or Neighborhood components analysis. In an embodiment, neighbors may be selected using brute force calculated based on Euclidean distance from point of interest whose class label is unknown to points contained within training set. Distance may also be measured utilizing other norms including for example cosine similarity between vectors. In an embodiment, neighbors may be selected utilizing tree like data structures to determine distances from points of interest to points contained within training sets. In an embodiment, distances may be computed by plotting in "n-dimensional" space as defined by any suitable coordinate system including without limitation Cartesian and polar, an n-dimensional vector space, or the like, where points represent data values.

With continued reference to FIG. 1, k-nearest neighbors algorithms may select k values with varying values. Larger values of k may reduce the effect of noise on classification of neighbors while making explicit boundaries between classes less distinct. K values may be calculated utilizing heuristic techniques including hyperparameter optimization. K values may be calculated utilizing bootstrapping methods.

With continued reference to FIG. 1, classification utilizing k-nearest neighbor algorithms may be useful to select optimal providers and physical performance executors based on weighted contributions of datasets containing provider datums and physical performance datums. Distances between known datasets may be utilized to label subsequent datasets including user requests for providers and physical performance executors utilizing any of the methodologies as described herein. Such calculations may aid in selecting optimal providers and physical performance executors.

With continued reference to FIG. 1, physical performance instruction set generator module 130 is configured to generate at least a provider instruction set including at least a provider instruction set and at least a physical performance instruction set as a function of the at least a provider datum and the at least a physical performance datum and the at least an alimentary instruction set. Provider instruction set 136 as used herein is a data structure containing information for provider to prepare dietary request. Provider instruction set 136 may include user information including remittance information, preferred remittance methods, one or more physical addresses for a user, contact information such as telephone number and email address, and any other applicable information relating to a user. Provider instruction set 136 may include one or more user entries containing information such as user preference as to foods and ingredients contained within dietary request such as a preference for a steak to be cooked medium well or for salmon to be well done. Provider instruction set 136 may include user entries including information including a user's likes and dislikes such as a preference for roasted cauliflower but not boiled cauliflower. Provider instruction set 136 may include user entries including user selection of a meal and/or meals from a menu provided for by provider. For example provider instruction set 136 may include a specific breakfast user wants prepared such as oatmeal with blueberries from a menu generated by provider with a choice of five different breakfast options. Provider instruction set 136 may include information contained within dietary request from a user such as a constitutional restriction or user preference. For example, provider instruction set 136 may include information such as a constitutional restriction including a user's self-reported allergy to eggs or a user's inability to consume green vegetables while user is taking a blood thinning medication such as warfarin. Provider instruction set 136 may include user input such as a user's preference for a certain food or meal to contain certain condiments, sauces, and sides, such as for example French fries to be delivered with ketchup or a ham and swiss sandwich to be delivered with mustard. Provider instruction set 136 may include physical performance executor information including selected physical performance executor, contact information of physical performance executor, mode of transportation of physical performance executor, identification information as to physical performance executor such as name, or picture identification and the like. Provider instruction set 136 may include information such as where and how provider will hand over possession of dietary request to physical performance executor.

With continued reference to FIG. 1, physical performance instruction set 138 as used herein is a data structure containing information for physical performance executor to deliver dietary request. Physical performance instruction set 138 may include any information pertaining to a user as described above in reference to provider instruction set. Physical performance instruction set 138 may include one or more user entries including for example, a user preference for dietary request to arrive at a certain time, instructions as to what physical performance executor should do upon delivery such as ring user's doorbell or leave dietary request at user's doorstep. Physical performance instruction set 138 may include provider information including selected provider, address of provider where physical performance executor will pick up dietary request, contact information for provider such as phone number and email. Physical performance instruction set 138 may include directions as to how a dietary request should be handled and stored while under care and supervision of physical performance executor; for example frozen meals may need to be kept on dry ice while a freshly prepared hamburger may need to be kept in an insulated warming tray. Physical performance instruction set 138 may include information and directions as to where physical performance executor may meet provider to receive dietary request. For example, provider may prefer for physical performance executor to wait in executor's mode of transportation upon arrival at provider's kitchen for example, and provider may walk outside to executor's mode of transportation and deliver dietary request to executor there. In yet another non-limiting example, provider may prefer to have executor come inside and pick up dietary request in person.

With continued reference to FIG. 1, generating at least a provider instruction set and at least a physical performance instruction set may include receiving at least a user input datum. At least a user input datum as used herein may include any user data as it regards to at least a dietary request. In an embodiment, at least a user input datum may include a user constraint. A user constraint as used herein may include a user restriction and/or request pertaining to at least a dietary request. A user constraint may include a user restriction such as a certain time of day or day of the week that user needs to receive at least a dietary request. A user constraint may include a preference for a certain meal that at least a provider may prepare or a preference for a particular physical performance executor or for the physical performance executor to occur at a certain time or location. Generating the at least a provider instruction set and at least a physical performance instruction set may include receiving the at least a user constraint, selecting at least a provider and at least a physical performance executor as a function of the at least a constraint, and transmitting a subset of data associated with the at least a user to the at least a provider and the at least a physical performance executor. In an embodiment, a provider and/or a physical performance executor may be selected who can fulfill the user constraint. For example, a user with a constraint such as a delivery of at least a dietary request by a certain time at night after work may then have at least a provider selected who can prepare the user's dietary request and prepare the dietary request with enough time for the at least a physical performance executor to deliver the dietary request to the user by the user's predetermined time. At least a provider and/or at least a physical performance executor who are unable to comply with user's constraint may not be selected for the user.

With continued reference to FIG. 1, system 100 includes a client interface module 140. Client interface module 140 may include any suitable hardware or software module. Client interface module 176 may be designed and configured to transmit and receive inputs and outputs from a user client device 142. A user client device 142 may include, without limitation, a display in communication with server 102; display may include any display as described in this disclosure. A user client device 142 may include an additional computing device, such as a mobile device, laptop, desktop, computer or the like. Output such as a provider instruction set may be displayed on at least a user client device 142 using for example second GUI 126.

With continued reference to FIG. 1, system 100 includes a provider network 144. Provider network 144 may include any provider. Provider may include any of the providers as described above. Provider network 144 may include at least a provider server which may include any server as disclosed herein throughout this disclosure. The at least a provider server may include any computing device suitable use as the at least a server 102. Provider network 144 may include at least a provider database which may include any database or datastore as disclosed in this disclosure. Although only a single provider network 144 is depicted, system 100 may be configured to involve multiple provider networks or various performances within a particular provider network. Provider network 144 is described in more detail below in reference to FIG. 16.

With continued reference to FIG. 1, system 100 includes a physical performance entity network 146. Physical performance entity network 146 may include at least a physical performance entity. Physical performance entity may include any physical performance executor. Physical performance executor may include any of the physical performance executors as described above, including any transportation channel that executes the physical performance instruction set. Physical performance entity network 146 may include at least a physical performance server which may include any server as disclosed herein throughout this disclosure. The at least a physical performance server may include any computing device suitable for use as the at least a server 102. Physical performance entity network 146 may include at least a physical performance entity database which may include any database or datastore as disclosed in this disclosure. Although only a single physical performance entity network 146 is depicted, system 100 may be configured to involve multiple physical performance entity networks or various performances within a particular physical performance entity network. Physical performance entity network 146 is described in more detail below in reference to FIG. 16.

Figure 2:
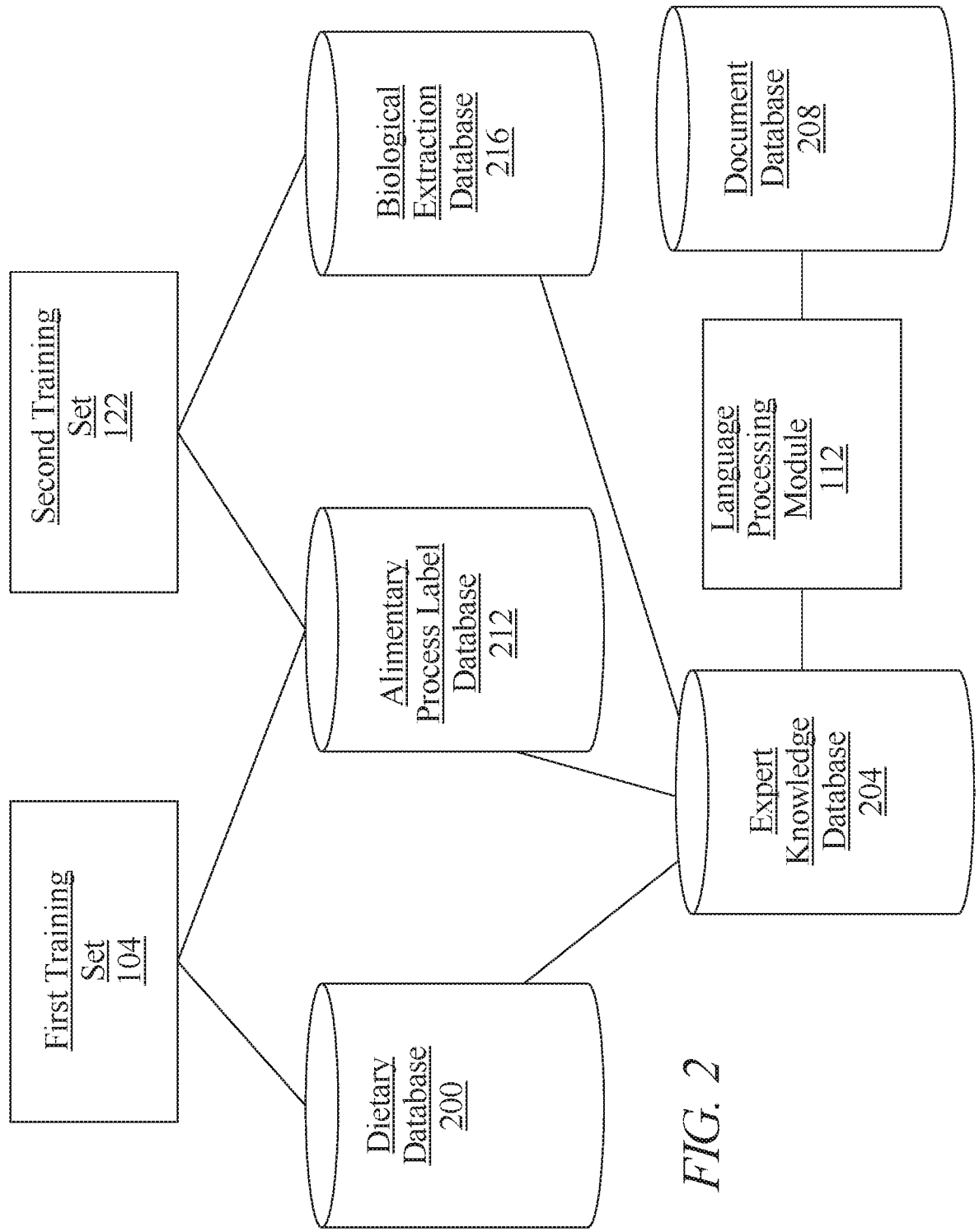
FIG. 2 is a block diagram illustrating embodiments of data storage facilities for use in disclosed systems and methods.

Referring now to FIG. 2, data incorporated in first training set 104 and/or second training set 122 may be incorporated in one or more databases. As a non-limiting example, one or more elements of dietary data may be stored in and/or retrieved from dietary data database. A dietary data database 200 may be implemented, without limitation, as a relational database, a key-value retrieval datastore such as a NOSQL database, or any other format or structure for use as a datastore that a person skilled in the art would recognize as suitable upon review of the entirety of this disclosure. A dietary data database 200 may include a plurality of data entries and/or records corresponding to elements of dietary data as described above. Data entries and/or records may describe, without limitation, data concerning particular dietary requests that have been collected; entries may describe particular foods and/or ingredients that are compatible with one or more dietary requests, which may be listed with related alimentary labels. For example, a dietary request for a gluten free diet and an unrelated dietary request for a Mediterranean diet may both may both be compatible with ingredients that include wild fish, grains such as buckwheat, polenta, and millet, and fresh vegetables such as kale, spinach, and tomatoes. Data entries may include alimentary labels and/or other descriptive entries describing results of evaluation of past dietary requests, including alimentary labels that were associated with conclusions regarding likelihood of future dietary requests associated with an initial dietary request. Such conclusions may have been generated by system 100 in previous iterations of methods, with or without validation of correctness by medical professionals such as functional medicine doctors, functional dieticians, functional nutritionists, and the like. Data entries in a dietary data database 200 may be flagged with or linked to one or more additional elements of information, which may be reflected in data entry cells and/or in linked tables such as tables related by one or more indices in a relational database; one or more additional elements of information may include data associating a dietary request with one or more cohorts, including demographic groupings such as ethnicity, sex, age, income, geographical region, or the like. Additional elements of information may include one or more categories of dietary data as described above. Additional elements of information may include descriptions of particular methods used to obtain dietary data, such as without limitation collecting dietary data from experts utilizing expert reports, papers, and/or opinions from experts who practice in a particular field related to a particular dietary request. Persons skilled in the art, upon reviewing the entirety of this disclosure, will be aware of various ways in which data entries in a dietary data database 200 may reflect categories, cohorts, and/or populations of data consistently with this disclosure.

With continued reference to FIG. 2, server 102 may be configured to have a feedback mechanism. In an embodiment, server 102 may be configured to receive a first training set 104 generated by system 100. For example, data about a user that has been previously been analyzed by server 102 may be utilized in algorithms by first model 120 and/or second model 128. Such algorithms may be continuously updated as a function of such data. In yet another embodiment, data analyzed by language processing module 112 may be utilized as part of training data generating algorithms by first model 120 and/or second model 128 and/or any other machine learning process performed by server 102.

Figure 3:
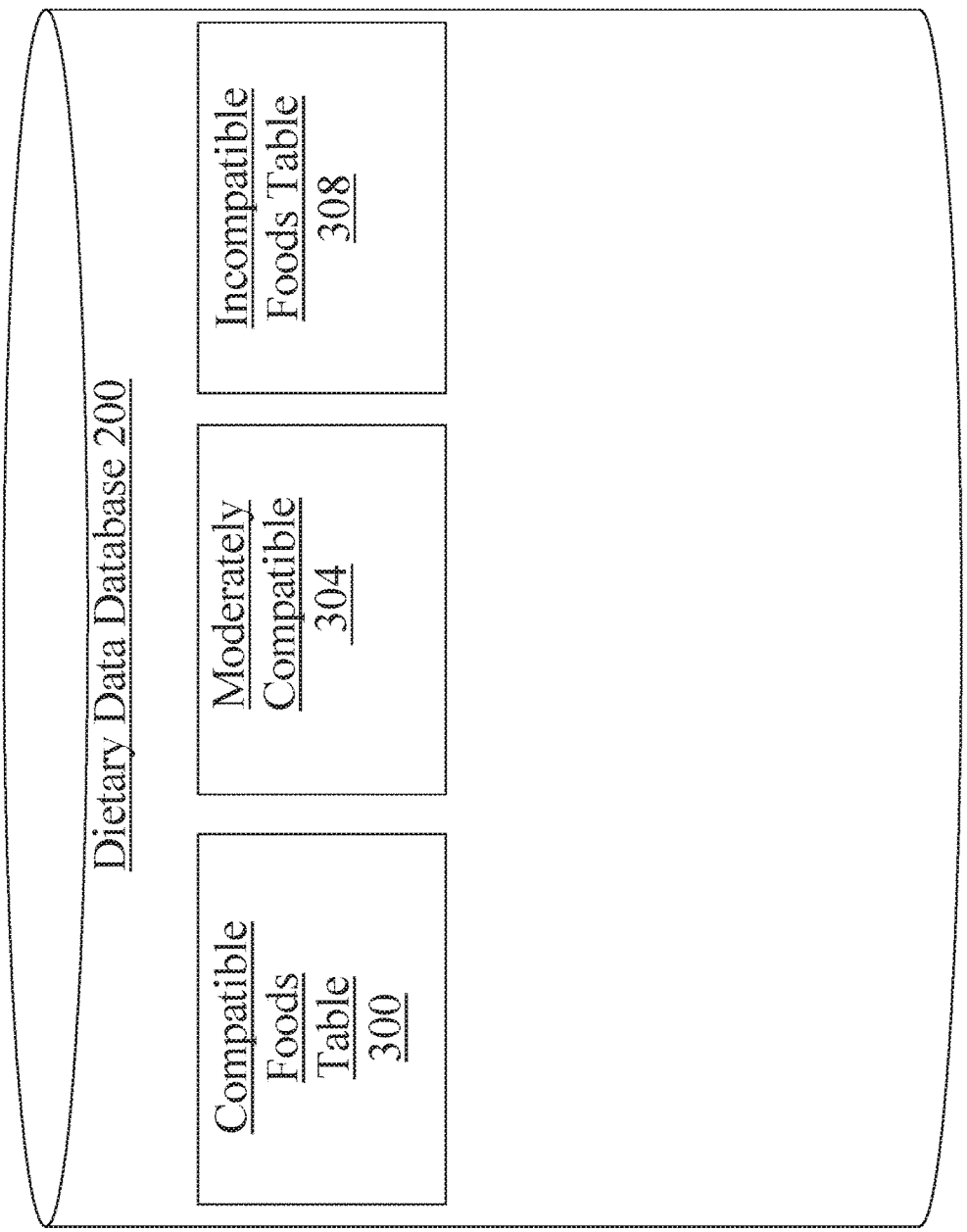
FIG. 3 is a block diagram illustrating an exemplary embodiment of a dietary data database.

Referring now to FIG. 3, an exemplary embodiment of dietary data database 200 is illustrated. One or more database tables in dietary data database 200 may include, as a non-limiting example, a compatible foods table 300. For instance and without limitation, compatible foods table 300 may be a table relating dietary requests to foods that are compatible with a particular dietary request; for instance where a dietary request contains a request for a ketogenic diet, foods such as beef tips, ground sirloin and lamb shanks may be compatible with such a request while such foods may not be compatible with a dietary request for a vegan diet. Dietary data database 200 may include moderately compatible food table 304 which may be a table relating dietary request to foods that are moderately compatible with a particular dietary request; for instance where a dietary request contains a request for a gluten free diet from a user with a self-reported gluten intolerance, foods such as certified gluten free oats may be moderately compatible with such a user, while certified gluten free oats may not be compatible for a user following a gluten free diet because of a previous diagnosis of Celiac Disease. For instance and without limitation, dietary data database 200 may include as a non-limiting example, incompatible food table 308. For instance and without limitation, incompatible food table 308 may include a table relating dietary requests to foods that are incompatible with a particular dietary request; for instance where a dietary request contains a request for a corn free diet ingredients such as cornstarch, corn oil, dextrin, maltodextrin, dextrose, fructose, ethanol, maize, and/or sorbitol may be listed. In an embodiment, database tables contained within dietary data database 200 may include groupings of foods by different categories such as grains, meats, vegetables, fruits, sugars and fats, and the like. In an embodiment, database tables contained within dietary data database 200 may include groups of foods by ingredients that a food may be comprised of, for example gravy may contain flour which may contain gluten.

Referring again to FIG. 2, server 102 and/or another device in system 100 may populate one or more fields in dietary data database 200 using expert information, which may be extracted or retrieved from an expert knowledge database 204. An expert knowledge database 204 may include any data structure and/or data store suitable for use as dietary data database 200 as described above. Expert knowledge database 204 may include data entries reflecting one or more expert submissions of data such as may have been submitted according to any process described above in reference to FIG. 1, including without limitation by using first graphical user interface 110 and/or second graphical user interface 126. Expert knowledge database may include one or more fields generated by language processing module 112, such as without limitation fields extracted from one or more documents as described above. For instance, and without limitation, one or more categories of dietary data and/or related alimentary labels and/or categories of alimentary labels associated with an element of physiological state data as described above may be stored in generalized from in an expert knowledge database 204 and linked to, entered in, or associated with entries in a dietary data database 200. Documents may be stored and/or retrieved by server 102 and/or language processing module 112 in and/or from a document database 208; document database 208 may include any data structure and/or data store suitable for use as dietary data database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 4:
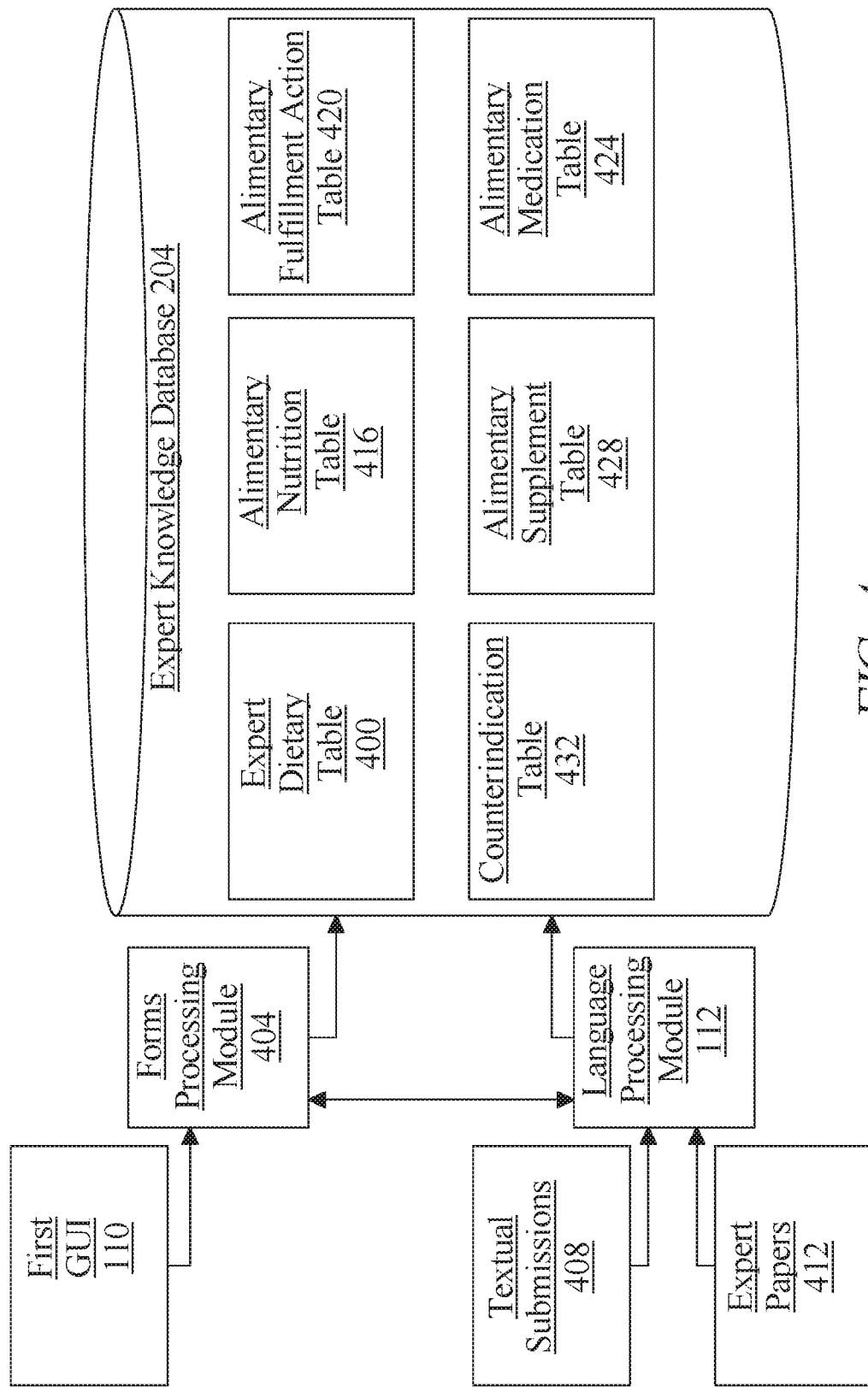
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 204 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert dietary table 400. Expert dietary table 400 may be a table relating dietary data as described above to alimentary labels; for instance, where an expert has entered data relating an alimentary label to a category of dietary data and/or to an element of dietary data via first graphical user interface 110 as described above, one or more rows recording such an entry may be inserted in expert dietary table 400. In an embodiment, a forms processing module 404 may sort data entered in a submission via first graphical user interface 110 by, for instance, sorting data from entries in the first graphical user interface 110 to related categories of data; for instance, data entered in an entry relating in the first graphical user interface 110 to an alimentary label may be sorted into variables and/or data structures for storage of alimentary labels, while data entered in an entry relating to a category of dietary data and/or an element thereof may be sorted into variables and/or data structures for the storage of, respectively, categories of dietary data or elements of dietary data. Where data is chosen by an expert from pre-selected entries such as drop-down lists, data may be stored directly; where data is entered in textual form, language processing module 112 may be used to map data to an appropriate existing label, for instance using a vector similarity test or other synonym-sensitive language processing test to map dietary data to an existing label. Alternatively or additionally, when a language processing algorithm, such as vector similarity comparison, indicates that an entry is not a synonym of an existing label, language processing module may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 112. Data may be extracted from expert papers 412, which may include without limitation publications in medical and/or scientific journals, by language processing module 112 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert dietary table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a further non-limiting example tables listing one or more alimentary process labels; expert data populating such tables may be provided, without limitation, using any process described above, including entry of data from first graphical user interface 110 via forms processing module 404 and/or language processing module 112, processing of textual submissions 408, or processing of expert papers 412. For instance, and without limitation, an alimentary nutrition table 416 may list one or more alimentary recommendations based on nutritional instructions, and/or links of such one or more alimentary recommendations to alimentary labels, as provided by experts according to any method of processing and/or entering expert data as described above. As a further example an alimentary fulfillment action table 420 may list one or more alimentary processes based on instructions for fulfillment actions a user should take, including without limitation fulfillment actions such as purchasing groceries at a grocery store, ordering groceries online, ordering a meal at a restaurant, cooking a meal at home, ordering a meal delivery kit, cooking a meal delivery kit, hiring a chef to prepare meals, and/or links of such one or more dietary requests to alimentary labels, as provided by experts according to any method of processing and/or entering expert data as described above. As an additional example, an alimentary supplement table 428 may list one or more alimentary processes based on nutritional supplements, such as vitamin pills or the like, and/or links of such one or more dietary requests to alimentary labels, as provided by experts according to any method of processing and/or entering expert data as described above. Alimentary supplement table 428 may list a recommended supplement a user may consider taking as a function of a dietary request. For example, a dietary request such as a vegan diet may be recommended to supplement with B vitamins. As a further non-limiting example, an alimentary medication table 424 may list one or more alimentary processes based on medications, including without limitation over-the-counter and prescription pharmaceutical drugs, and/or links of such one or more dietary requests to alimentary labels, as provided by experts according to any method of processing and/or entering expert data as described above. Alimentary medication table 424 may recommend a dietary request as a function of a medication a user may be taking. For example, a user taking an antibiotic such as metronidazole may be recommended to eliminate alcohol, while a user taking a medication such as doxycycline may be recommended to eliminate dairy containing products. As an additional example, a counterindication table 432 may list one or more counterindications for one or more dietary requests; counterindications may include, without limitation allergies to one or more foods, medications, and/or supplements, side-effects of one or more medications and/or supplements, interactions between medications, foods, and/or supplements, exercises that should not be used given one or more dietary request.

Referring now to FIG. 2, system 100 may include or communicate with an alimentary process label database 212; an alimentary process label database 212 may include any data structure and/or datastore suitable for use as a dietary data database 200 as described above. An alimentary process label database 212 may include one or more entries listing labels associated with one or more alimentary processes as described above, including any dietary requests correlated with alimentary labels in first training set 104 as described above; alimentary process labels may be linked to or refer to entries in alimentary label database 212 to which alimentary process labels correspond. Linking may be performed by reference to historical data concerning alimentary labels, such as ingredients, products, food items, lifestyle, and/or dietary choices associated with dietary requests in the past; alternatively or additionally, a relationship between an alimentary process label and a data entry in alimentary process label database 212 may be determined by reference to a record in an expert knowledge database 204 linking a given alimentary process label to a given category of alimentary label as described above. Entries in alimentary process label database 212 may be associated with one or more categories of alimentary labels as described above, for instance using data stored in and/or extracted from an expert knowledge database 204.

With continued reference to FIG. 2, first training set 104 may be populated by retrieval of one or more records from dietary data database 200 and/or alimentary process label database 212; in an embodiment, entries retrieved from dietary data database 200 and/or alimentary process label database 212 may be filtered and or select via query to match one or more additional elements of information as described above, so as to retrieve a first training set 104 including data belonging to a given cohort, demographic population, or other set, so as to generate outputs as described below that are tailored to a person or persons with regard to whom system 100 classifies dietary requests to alimentary labels as set forth in further detail below. Persons skilled in the art, upon reviewing the entirety of this disclosure, will be aware of various ways in which records may be retrieved from dietary data database 200 and/or alimentary process label database 212 to generate a training set to reflect individualized group data pertaining to a person of interest in operation of system and/or method, including without limitation a person with regard to whom at least a dietary request is being evaluated. Server may alternatively or additionally receive a first training set 104 and store one or more entries in dietary database 200 and/or alimentary process label database 212 as extracted from elements of first training set 104.

With continued reference to FIG. 2, first training set 104 may be populated by matching user entries with dietary requests. For example, first training set 104 may be populated by analyzing user entries such as by language processing module 112 to analyze what types of meals and/or food choices that a user made. User entries as described in more detail below, may be received by server 102 such as from user client device 142. In an embodiment, user may generate user entries at first GUI 110, second GUI 126, and/or client interface module 140. User entries may then be matched against an associated dietary request. For example, a user entry for a dietary request such as a vegan diet may be analyzed by language processing module 112 to determine what previous providers were able to be selected that could fulfill user's request. In yet another non-limiting example, a user entry for a dietary request such as a gluten free diet may be analyzed by language processing module 112 to determine alimentary process label 108 that dietary input may be matched with. Such data may then be utilized as first training set 104. First training set 104 may also be obtained by performing a loss function and optimizing roots as described in more detail below.

With continued reference to FIG. 2, server 102 may receive an update to one or more elements of data represented in first training set 104 and may perform one or more modifications to first training set 104, or to dietary data database 200, expert knowledge database 204, and/or alimentary process label database 212 as a result. For instance, a dietary request may turn out to have been erroneously recorded such as when a user requested a dietary request but mere seconds later revoked such a request; server 102 may remove it from first training set 104, dietary data database 200, expert knowledge database 204, and/or alimentary process label database 212 as a result. As a further example, a medical and/or academic paper, or a study on which it was based, may be revoked; server 102 may remove it from first training set 104, dietary data database 200, expert knowledge database 204, and/or alimentary process label database 212 as a result. Information provided by an expert may likewise be removed if the expert loses credentials or is revealed to have acted fraudulently.

Continuing to refer to FIG. 2, elements of data first training set 104, dietary database 200, expert knowledge database 204, and/or alimentary process label database 212 may have temporal attributes, such as timestamps; server 102 may order such elements according to recency, select only elements more recently entered for first training set 104 and/or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

With continued reference to FIG. 2, data incorporated in second training set 122 may be incorporated in one or more databases. As a non-limiting example, one or more elements of biological extraction data may be stored in and/or retrieved from a biological extraction database 216. Biological extraction database 216 may include any database or datastore structure as described herein.

Figure 5:
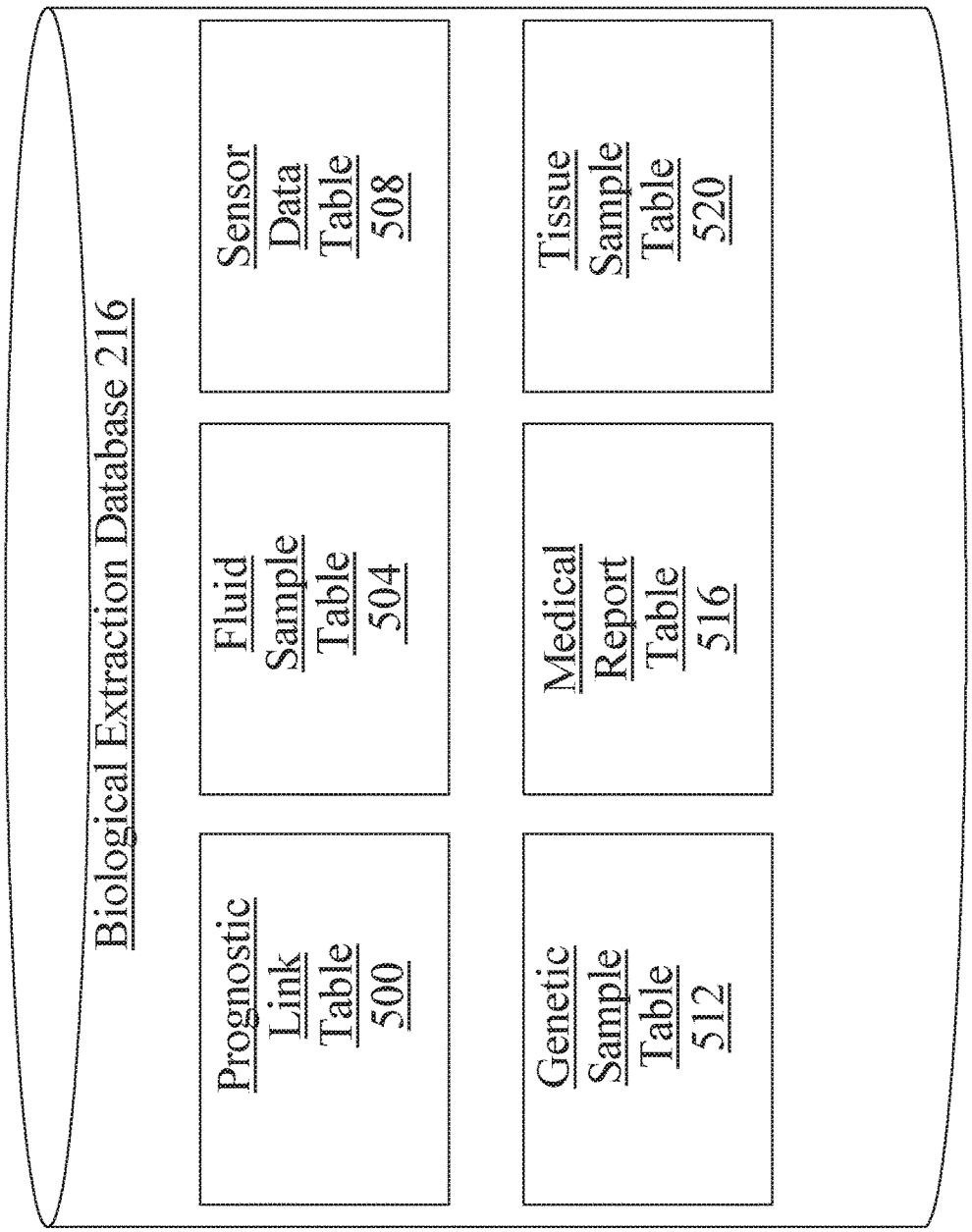
FIG. 5 is a block diagram illustrating an exemplary embodiment of a biological extraction database.

Referring now to FIG. 5, an exemplary embodiment of biological extraction database 216 is illustrated. Biological extraction database 216 may include as a non-limiting example, prognostic link table 500. Prognostic link table 500 may be a table relating biological extraction data to a prognostic label; for instance, where an expert has entered data relating a prognostic label to a category of biological extraction data, such information may be contained within prognostic link table 500. Biological extraction database 216 may include a fluid sample table 504 listing samples acquired from a person by extraction of fluids, such as without limitation, blood, lymph cerebrospinal fluid, or the like. As another non-limiting example, biological extraction database 216 may include a sensor data table 508, which may list samples acquired using one or more sensors, for instance as described in further detail below. As a further non-limiting example, biological extraction database 216 may include a genetic sample table 512, which may list partial or entire sequences of genetic material. Genetic material may be extracted and amplified, as a non-limiting example, using polymerase chain reactions (PCR) or the like. As a further example, also non-limiting, biological extraction database 216 may include a medical report table 516, which may list textual descriptions of medical tests, including without limitation radiological tests or tests of strength and/or dexterity or the like. Data in medical report table may be sorted and/or categorized using language processing module 112, for instance, translating a textual description into a numerical value and a label corresponding to a category of biological extraction data; this may be performed using any language processing algorithm or algorithms as described in this disclosure. As another non-limiting example, biological extraction database 216 may include a tissue sample table 520, which may record biological extraction data obtained using tissue samples. Tables presented above are presented for exemplary purposes only; persons skilled in the art will be aware of various ways in which data may be organized in biological extraction database 216 consistently with this disclosure.

Figure 6:
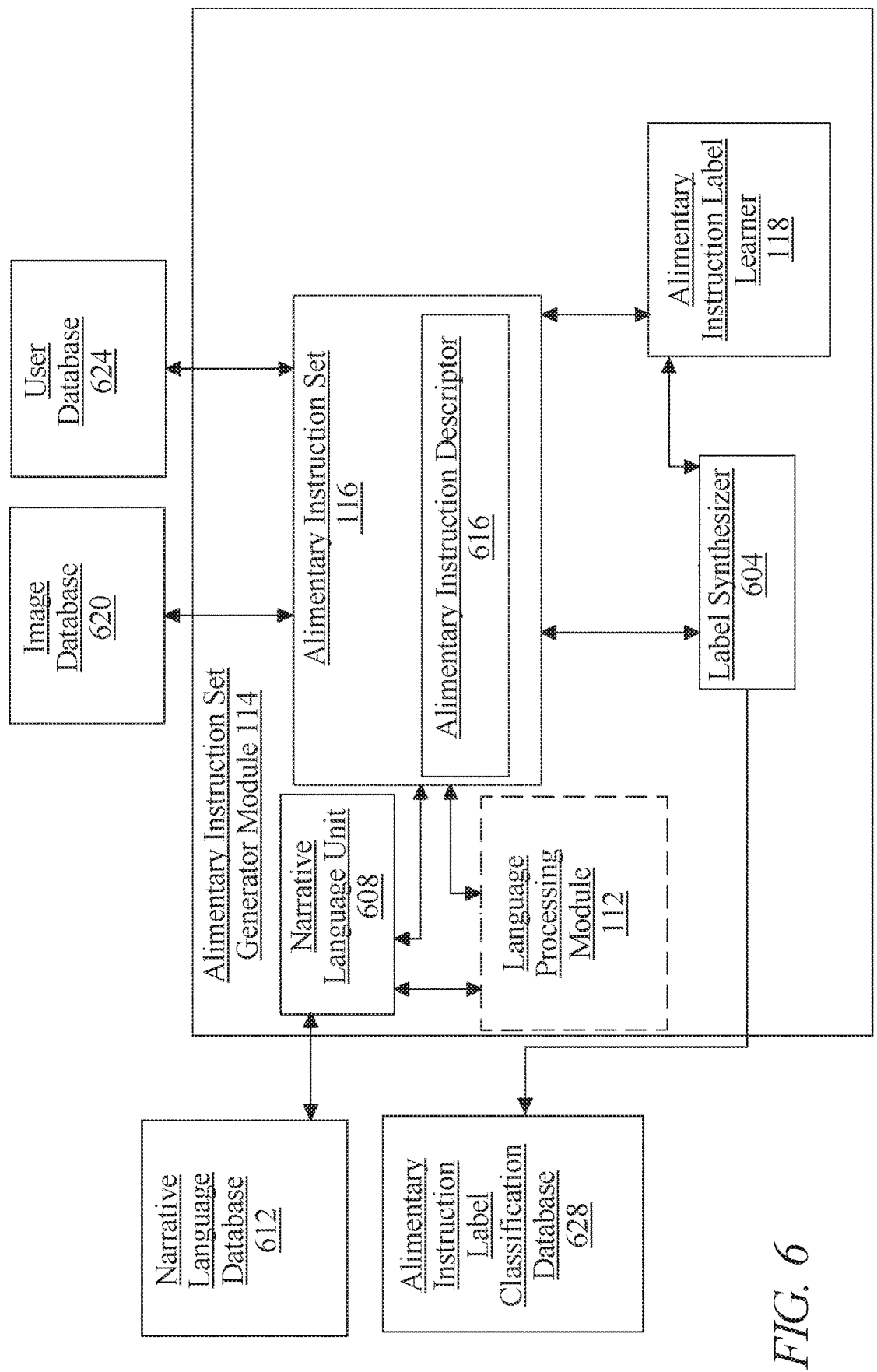
FIG. 6 is a block diagram illustrating an exemplary embodiment of an alimentary instruction set generator module.

Referring now to FIG. 6, an exemplary embodiment of alimentary instruction set generator module is illustrated. Alimentary instruction set generator module 114 is designed and configured to generate at least an alimentary instruction set as a function of the at least a dietary request. Alimentary instruction set may include any of the alimentary instruction sets as described above. In an embodiment, alimentary instruction set generator module 114 may generate alimentary instruction set 116 based on integration of data associated with first training set 104, second training set 122 any applicable external sources, and any applicable database within system 100. Generation of alimentary instruction set 116 may include identification of one or more alimentary instruction sets as a function of dietary request including for example a user input datum such as a constitutional restriction, user preference, and the like. Generation of alimentary instruction set 116 may include identification of one or more alimentary instruction sets as a function of biological extraction data. Generation of alimentary instruction set 116 may include identification of one or more alimentary instructions and insertion of the one or more alimentary instructions in the alimentary instruction set 116. For example, alimentary instruction set 116 may be formed, wholly or partially, by aggregating alimentary instructions and combining the aggregated alimentary instructions using narrative language module, narrative language database, image database, or the like as described in more detail below.

With continued reference to FIG. 6, alimentary instruction set generator module 114 may include a label synthesizer 604. Label synthesizer 604 may include any suitable software or hardware module. In an embodiment, label synthesizer 604 may be designed and configured to combine a plurality of labels in at least an alimentary process label together to provide maximally efficient data presentation. Combination of labels together may include elimination of duplicate information. For instance, label synthesizer 604 and/or at least a server 102 may be designed and configure to determine a first alimentary label of the at least an alimentary label is a duplicate of a second alimentary label of the at least an alimentary label and eliminate the first alimentary label. Determination that a first alimentary label is a duplicate of a second alimentary label may include determining that the first alimentary label is identical to the second alimentary label; for instance, an alimentary label generated from test data presented in one dietary request of at least a dietary request may be the same as an alimentary label generated from test data presented in a second dietary request of at least a dietary request. As a further non-limiting example, a first alimentary label may be synonymous with a second alimentary label, where detection of synonymous labels may be performed, without limitation, by a language processing module 112 as described above.

Continuing to refer to FIG. 6, label synthesizer 604 may group alimentary labels according to one or more classification systems relating the alimentary labels to each other. For instance, alimentary instruction set generator module 114 and/or label synthesizer 604 may be configured to determine that a first alimentary label of the at least an alimentary label and a second alimentary label of the at least an alimentary label belong to a shared category. A shared category may be an ingredient, food and/or or category of food or ingredient to which each of first alimentary label and second alimentary label belongs; as an example, lactose free diet and dairy free diet may be examples of dietary requests which may in turn share of a category of food ingredients such as milk alternatives including coconut milk, almond milk, hemp milk, oat milk, and/or soy milk.

With continued reference to FIG. 6, alimentary data may be identified and aggregated into a subset of applicable alimentary data based on at least a dietary request and first training set 104. Alimentary data may be identified and aggregated into a subset of applicable alimentary data based on at least a biological extraction data and second training set 122. In an embodiment, alimentary instruction set 116 may comprise a plurality of alimentary data specific to user that is able to be used by machine learning and artificial intelligence systems in order to continuously update or modify training sets, and alimentary instruction set 116 based on updated or progressions associated with implementation of alimentary instruction set 116 by user. Alimentary data and non-alimentary data may include compilations of instruction sets received over a period of time, the compilations may account for improvements or modifications associated with user. Alimentary instruction set 116 may further include instructions over time, in which the alimentary instructions may change in response to changes in a user's data and/or prognosis. Alternatively or additionally, system 100 may periodically iterate through one or more processes as described in this disclosure, such that repeated reevaluations may modify alimentary instruction set 116 as information concerning user and/or dietary requests obtained from the user change over time.

With continued reference to FIG. 6, in one embodiment, alimentary instruction set generator module 114 may be configured to generate alimentary instruction set process descriptor 616 by converting one or more alimentary instruction set labels into narrative language. As a non-limiting example, alimentary instruction set generator module 114 may include and/or communicate with narrative language unit 608, which may be configured to determine an element of narrative language associated with at least an alimentary instruction set label and include the element of narrative language in current alimentary instruction set label descriptor. Narrative language unit 608 may implement this, without limitation, by using a language processing module 112 to detect one or more associations between alimentary instruction set labels, or lists of alimentary instruction set labels, and phrases and/or statements of narrative language. Alternatively or additionally, narrative language unit 608 may retrieve one or more elements of narrative language from narrative language database 612, which may contain one or more tables associating alimentary instruction set labels and/or groups of alimentary instruction set labels with words, sentences, and/or phrases of narrative language. One or more elements of narrative language may be included in alimentary instruction set, for instance for display to a user as text describing a current alimentary instruction set status of the user. Alimentary instruction set process descriptor 616 may further include one or more images; one or more images may be retrieved by alimentary instruction set generator module from an image database 620, which may contain one or more tables associating alimentary instruction set labels, groups of alimentary instruction set labels, alimentary instruction set process descriptors 616, or the like with one or more images.

With continued reference to FIG. 6, in an embodiment, relationships between alimentary labels and categories may be retrieved from an alimentary instruction label classification database 628, for instance by generating a query using one or more alimentary labels of at least an alimentary output, entering the query, and receiving one or more categories matching the query from the alimentary instruction label classification database 628.

Figure 7:
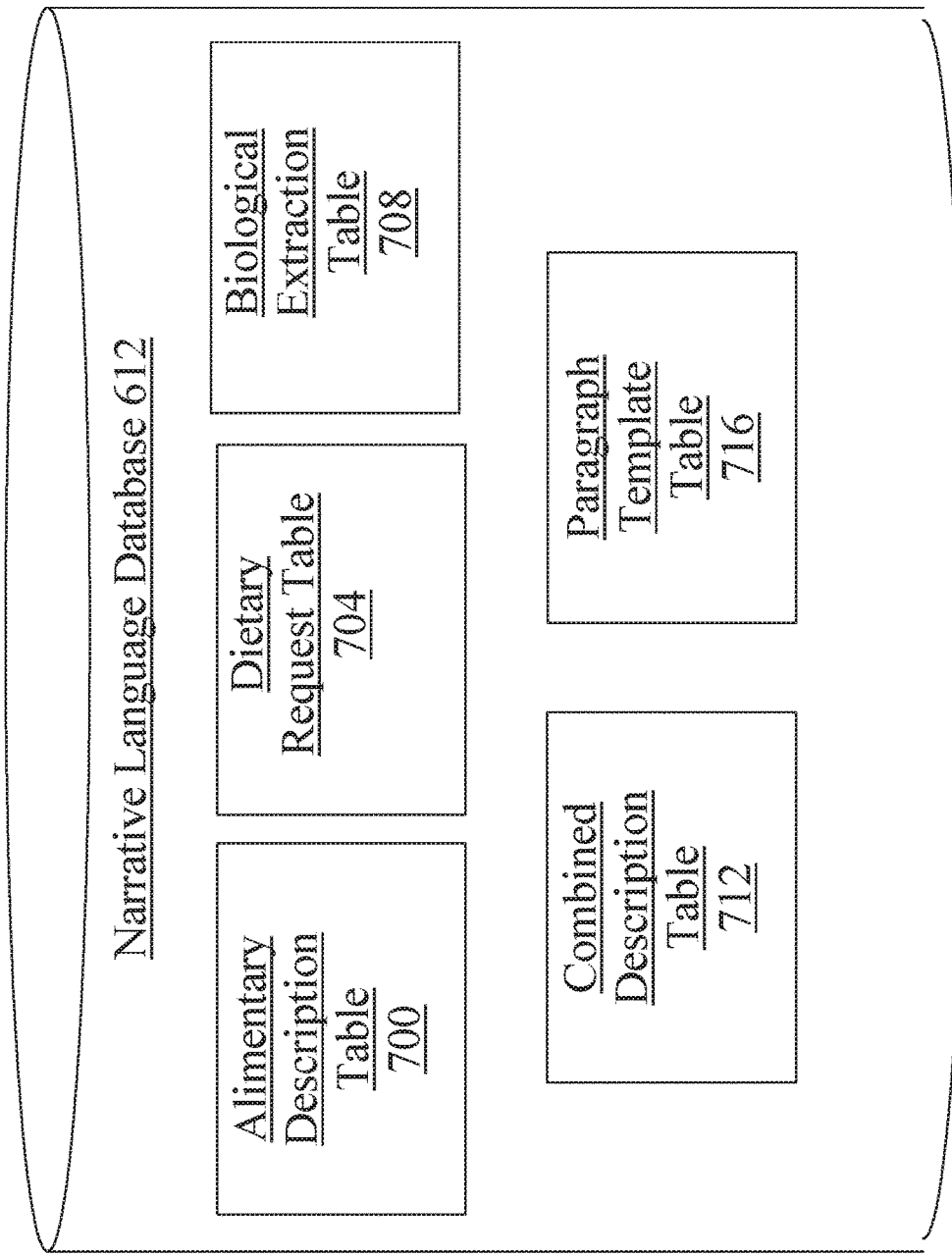
FIG. 7 is a block diagram illustrating an exemplary embodiment of a narrative language database.

Referring now to FIG. 7, an exemplary embodiment of narrative language database 612 is illustrated. Narrative language database 612 may be implemented as any database and/or datastore suitable for use as biological extraction database 216 as described above. One or more database tables in narrative language database 612 may include, without limitation, an alimentary description table 700, which may link alimentary labels to narrative descriptions associated with alimentary labels. One or more database tables in narrative language database 612 may include, without limitation, a dietary request table 704, which may link dietary requests to narrative descriptions associated with alimentary process labels. One or more database tables in narrative language database 612 may include, without limitation, a biological extraction table 708, which may link biological extractions to narrative descriptions associated with alimentary process labels. One or more database tables in narrative language database 612 may include, without limitation, a combined description table 712, which may link combinations of dietary requests and alimentary labels as well as biological extractions and alimentary labels to narrative descriptions associated with the combinations. One or more database tables in narrative language database 612 may include, without limitation, a paragraph template table 716, which may contain one or more templates of paragraphs, pages, reports, or the like into which images and text, such as images obtained from image database 620 and text obtained from alimentary description table 700, dietary request table 704, biological extraction table 708, and combined description table 712 may be inserted. Tables in narrative language database 612 may be populated, as a non-limiting example, using submissions from experts, which may be collected according to any processes described above. Persons skilled in the art, upon reviewing the entirety of this disclosure, will be aware of various ways in which entries in narrative language database 612 may be categorized and/or organized.

Figure 8:
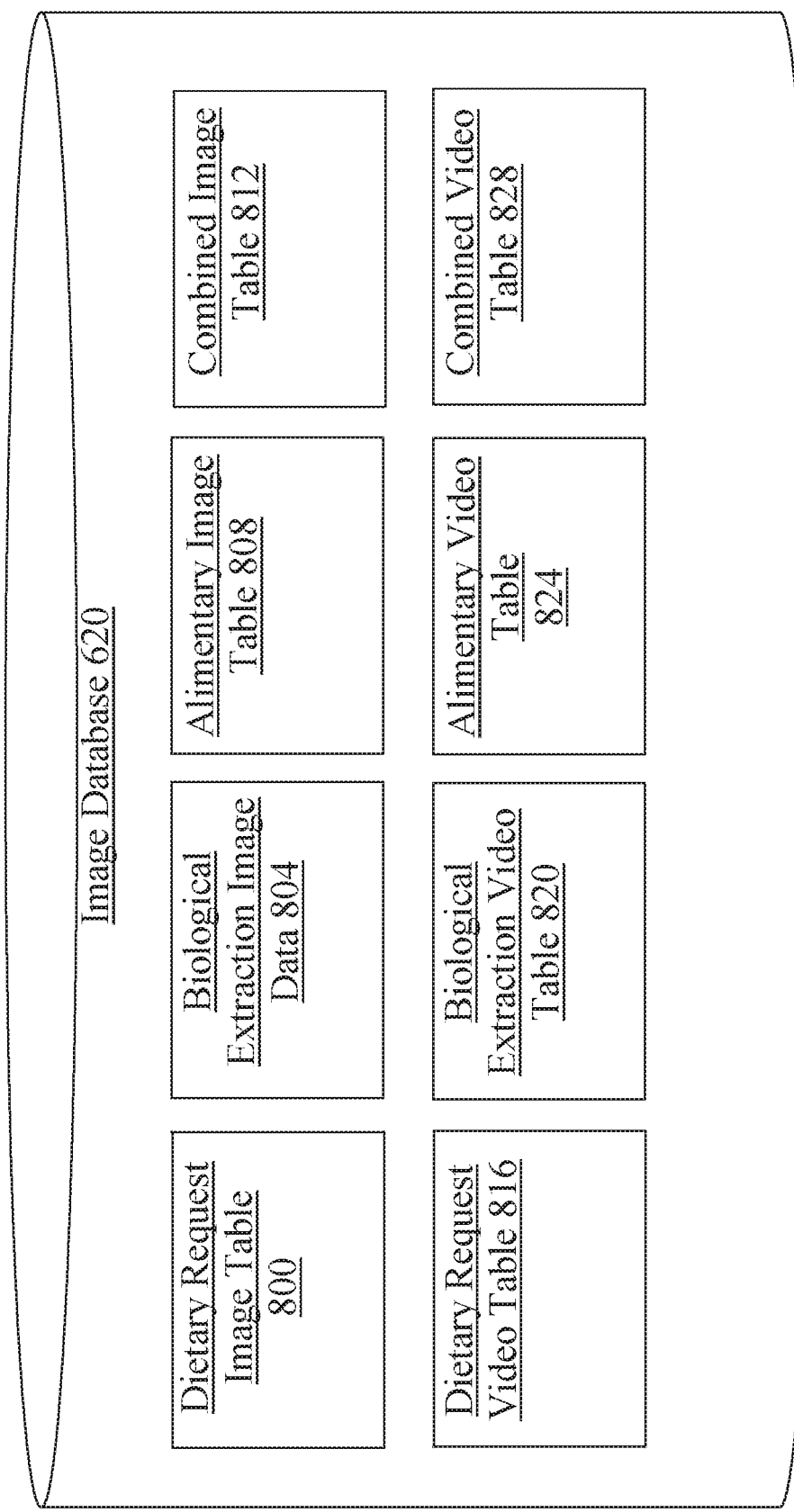
FIG. 8 is a block diagram illustrating an exemplary embodiment of an image database.

Referring now to FIG. 8, an exemplary embodiment of image database 620 is illustrated. Image database 620 may be implemented as any database and/or datastore suitable for use as dietary database 200 as described above. One or more database tables in image database 620 may include, without limitation, a dietary request image table 800, which may link dietary requests to images associated with alimentary labels. One or more database tables in image database 620 may include, without limitation, a biological extraction image table 804, which may link biological extractions to images associated with alimentary process labels. One or more database tables in image database 620 may include, without limitation, an alimentary image table 808, which may link alimentary process labels to images associated with alimentary process labels. One or more database tables in image database 620 may include, without limitation, a combined description table 812, which may link combinations of dietary requests, biological extractions and alimentary labels to images associated with the combinations. One or more database tables in image database 620 may include, without limitation, a dietary request video table 816, which may link dietary requests to videos associated with alimentary labels. One or more database tables in image database 620 may include, without limitation, a biological extraction video table 820, which may link biological extractions to videos associated with alimentary process labels. One or more database tables in image database 620 may include, without limitation, an alimentary video table 824, which may link alimentary process labels to videos associated with alimentary process labels. One or more database tables in image database 620 may include, without limitation, a combined video table 828, which may link combinations of dietary requests, biological extractions and alimentary labels to videos associated with the combinations. Tables in image database 620 may be populated, without limitation, by submissions by experts, which may be provided according to any process or process steps described in this disclosure for collection of expert submissions.

Figure 9:
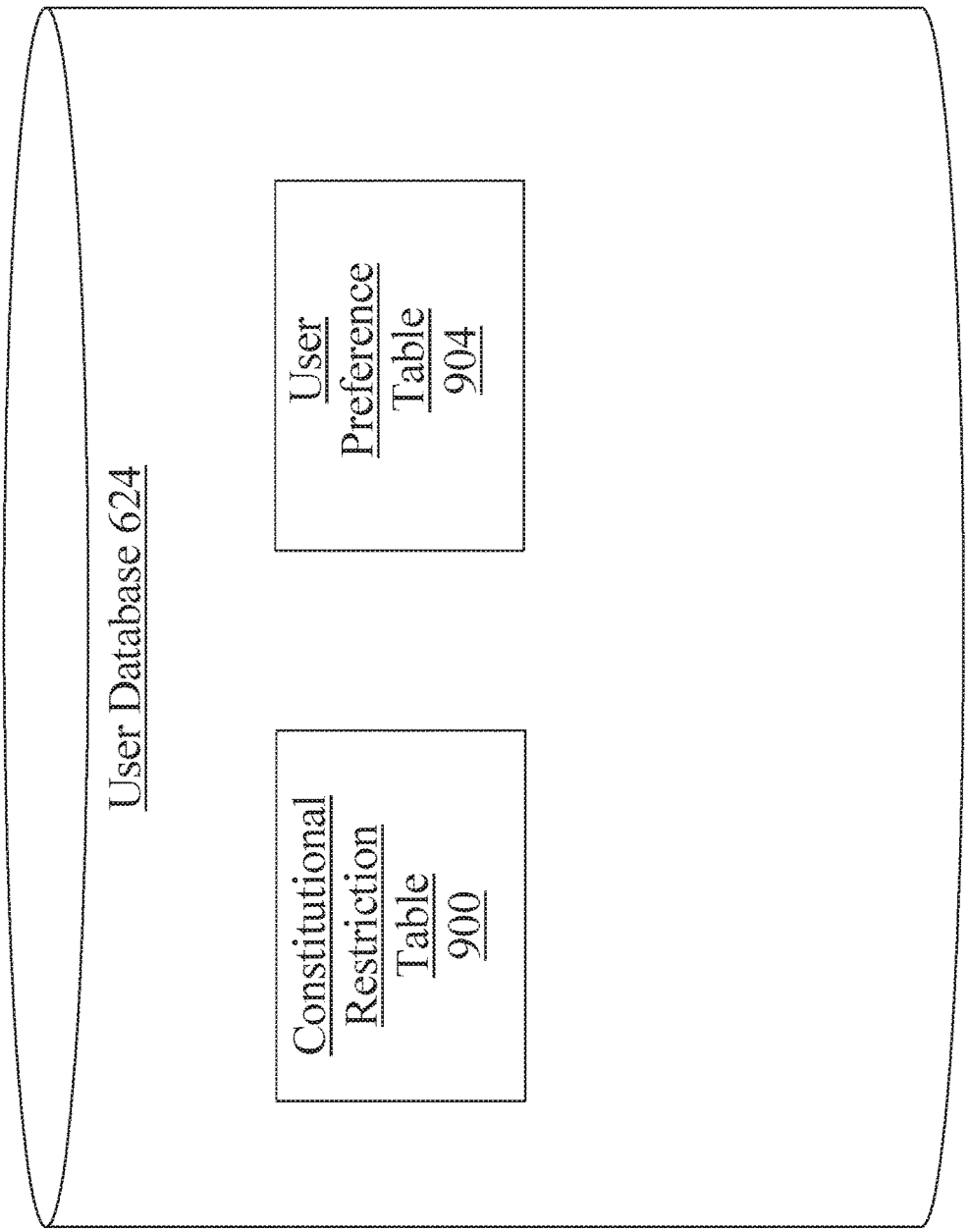
FIG. 9 is a block diagram illustrating an exemplary embodiment of a user database.

Referring now to FIG. 9, an exemplary embodiment of user database 624 is illustrated. User database 624 may be implemented as any database and/or datastore suitable for use as described above. One or more database tables in user database 624 may include, without limitation, a constitutional restriction table 900; at least a constitutional restriction may be linked to a given user and/or user identifier contained within a constitutional restriction table 900. One or more database tables in user database 624 may include, without limitation, a user preference table 904; at least a user preference may be linked to a given user and/or user identifier in a user preference table 904.

Figure 10:
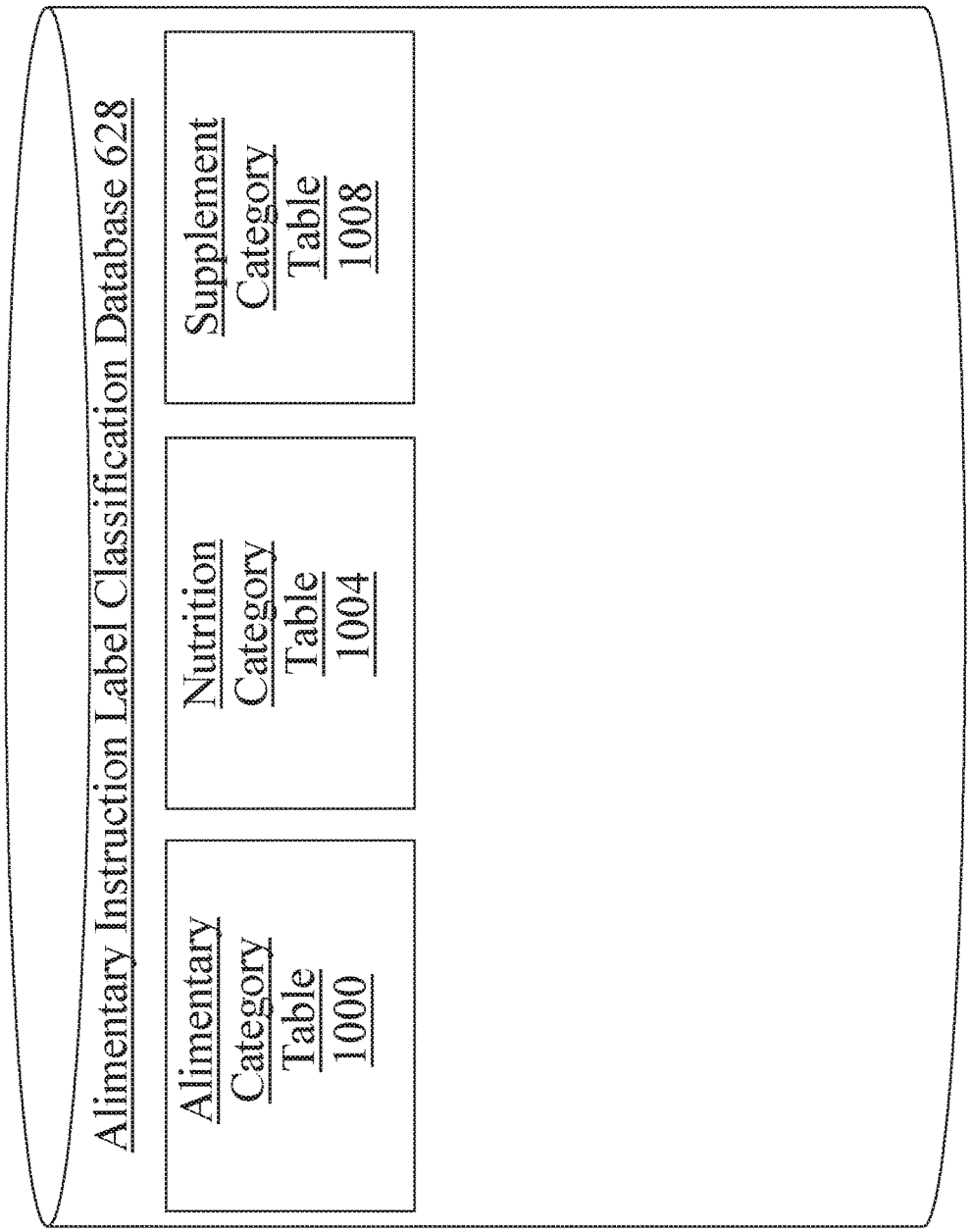
FIG. 10 is a block diagram illustrating an exemplary embodiment of an alimentary instruction label classification database.

Referring now to FIG. 10, an exemplary embodiment of an alimentary instruction label classification database 628 is illustrated. Alimentary instruction label classification database 628 may operate on the server 102. Alimentary instruction label classification database 628 may be implemented as any database and/or datastore suitable for use as a database. One or more database tables in alimentary instruction label classification database 628 may include, without limitation, an alimentary category table 1000; which may associate an alimentary instruction label with one or more categories of nutritional properties, ingredients, foodstuffs, or the like. One or more database tables in alimentary instruction label classification database 628 may include, without limitation, an nutrition category table 1004, which may describe one or more categories of nutrition, such as breakdown by fats, carbohydrates, protein, vegetables, fruits, and the like or nutrition categories such as breakdown by micronutrient such as calcium, Vitamin A, Vitamin D, iron, chromium and the like. One or more database tables in alimentary instruction label classification database 628 may include, without limitation, a supplement table 1008, which may describe a supplement that relates to a dietary request, such as a grain free diet with a recommendation for fiber supplementation or a vegetarian diet with a recommendation for B vitamin supplementation.

Figure 11:
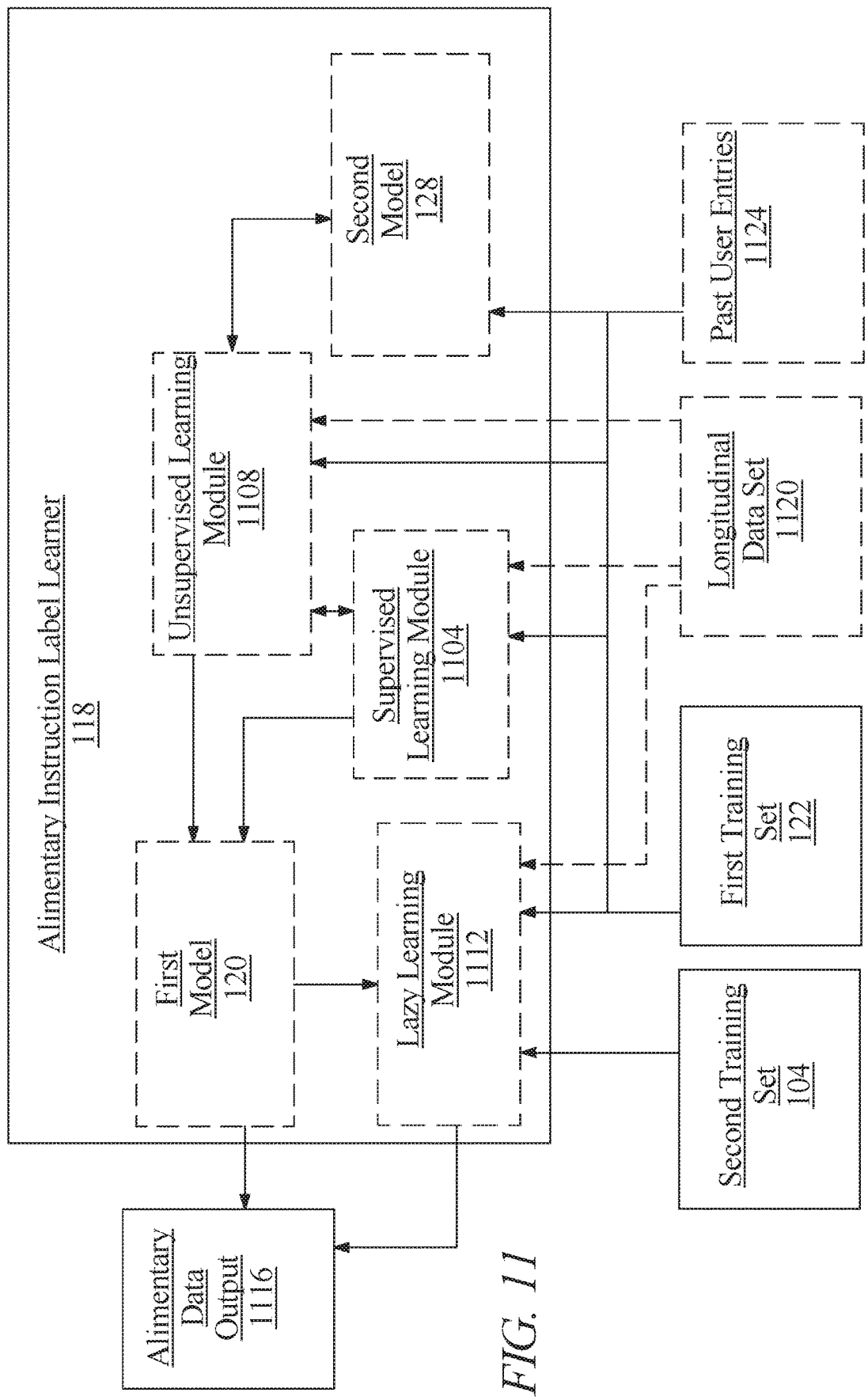
FIG. 11 is a block diagram illustrating an exemplary embodiment of an alimentary instruction label learner.

Referring now to FIG. 11, an exemplary embodiment of alimentary instruction label learner 118 is illustrated. Alimentary instruction label learner 118 may be configured to perform one or more supervised learning processes, supervised learning processes may be performed by a supervised learning module 1104 executing on server 102 and/or on another computing device in communication with server 102, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of dietary data as inputs, alimentary labels as outputs, and a scoring function representing a desired form of relationship to be detected between elements of dietary data and alimentary labels; scoring function may, for instance, seek to maximize the probability that a given element of dietary data and/or combination of elements of dietary data is associated with a given alimentary label and/or combination of alimentary labels to minimize the probability that a given element of dietary data and/or combination of elements of dietary data is not associated with a given alimentary label and/or combination of alimentary labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 104. Persons skilled in the art, upon reviewing the entirety of this disclosure, will be aware of various possible variations of supervised machine learning algorithms that may be used to determine relation between elements of dietary data and alimentary labels. In yet another non-limiting example, a supervised learning algorithm may use elements of biological extraction data as inputs, alimentary labels as outputs, and a scoring function representing a desired form of relationship to be detected between elements of biological extraction data and alimentary labels. For example, an input containing a biological extraction such as an elevated fasting glucose blood level may be related to an alimentary label that includes impaired carbohydrate metabolism. In an embodiment, one or more supervised machine-learning algorithms may be restricted to a particular domain for instance, a supervised machine-learning process may be performed with respect to a given set of parameters and/or categories of parameters that have been suspected to be related to a given set of alimentary labels, and/or are specified as linked to a particular field of dietary requests. As a non-limiting example, a particular set of foods and/or food groups may be typically consumed by certain diets such as for example, coconut meat consumed on a ketogenic diets or raw foods diet, and a supervised machine-learning process may be performed to relate those foods and/or food groups to the various dietary requests; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate alimentary labels. Additional supervised learning processes may be performed without domain restrictions to detect, for instance, previously unknown and/or unsuspected relationships between dietary data and alimentary labels.

With continued reference to FIG. 11, alimentary instruction label learner 118 may perform one or more unsupervised machine-learning processes as described above; unsupervised processes may be performed by an unsupervised learning module 1108 executing on server 102 and/or on another computing device in communication with server 102, which may include any hardware or software module. For instance, and without limitation, alimentary instruction label learner 118 and/or server 102 may perform an unsupervised machine learning process on first training set 104, which may cluster data of first training set 104 according to detected relationships between elements of the first training set 104, including without limitation correlations of alimentary labels to each other; such relations may then be combined with supervised machine learning results to add new criteria for alimentary instruction label learner 118 to apply in relating dietary data to alimentary labels. As a non-limiting, illustrative example, an unsupervised process may determine that a first dietary request correlates closely with a second dietary request, where the first dietary request has been linked via supervised learning processes to a given alimentary label, but the second has not; for instance, the second dietary request may not have been defined as an input for the supervised learning process, or may pertain to a domain outside of a domain limitation for the supervised learning process. Continuing the example, a close correlation between first dietary request and second dietary request may indicate that the second dietary request is also a good match for the alimentary label; second dietary request may be included in a new supervised process to derive a relationship or may be used as a synonym or proxy for the first dietary request by alimentary instruction label learner 118. Unsupervised processes performed by alimentary instruction label learner 118 may be subjected to any domain limitations suitable for unsupervised processes as described above.

Still referring to FIG. 11, server 102 and/or alimentary instruction label learner 118 may detect further significant categories of dietary requests, relationships of such categories to alimentary labels, and/or categories of alimentary labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to server 102, alimentary instruction label learner 118 and/or server 102 may continuously or iteratively perform unsupervised machine-learning processes to detect relationships between different elements of the added and/or overall data; in an embodiment, this may enable server 102 to use detected relationships to discover new correlations between known dietary requests, alimentary labels, and one or more elements of data in large bodies of data, such as nutritional, health, lifestyle, and/or dietary-related data, enabling future supervised learning and/or lazy learning processes to identify relationships between, e.g., particular dietary requests and particular alimentary labels. In an embodiment, use of unsupervised learning may greatly enhance the accuracy and detail with which system may detect alimentary labels.

Continuing to view FIG. 11, alimentary instruction label learner 118 may be configured to perform a lazy learning process as a function of the first training set 104 and the at least a dietary request to produce the at least an alimentary output; a lazy learning process may include any lazy learning process. Lazy learning processes may be performed by a lazy learning module 1112 executing on server 102 and/or on another computing device in communication with server 102, which may include any hardware or software module.

With continued reference to FIG. 11, alimentary instruction label learner 118 may generate a plurality of alimentary labels having different implications for a particular person. For instance, where a dietary request includes a request for a grain free diet, various dietary choices may be generated as alimentary labels associated with the dietary request, such as alimentary labels that may include protein choices such as lamb, veal, beef, chicken, cod, salmon, shrimp, and herring. In such an instance, alimentary instruction label learner 118 and/or server 102 may perform additional processes to resolve ambiguity. Processes may include presenting multiple possible results to a user, informing the user of various options that may be available, and/or that follow-up question may be required to select an appropriate choice such as asking a user what protein choices user prefers, likes, and/or dislikes. Alternatively or additionally, processes may include additional machine learning steps. For instance, alimentary instruction label learner 118 may perform one or more lazy learning processes using a more comprehensive set of user data to identify a more probably correct result of the multiple results. Alimentary instruction label learner 118 may generate alimentary data output 1116 as a function of first training set 104 and/or first model 116. Results may be presented and/or retained with rankings, for instance to advise a user of the relative probabilities of various alimentary labels being correct or ideal choices for a given user; alternatively or additionally, alimentary labels associated with a probability of success or suitability below a given threshold and/or alimentary labels contradicting results of the additional process, may be eliminated. As a non-limiting example, an additional process may reveal that a user is allergic to salmon, and consumption of salmon may be eliminated as an alimentary label to be presented.

Continuing to refer to FIG. 11, alimentary instruction label learner 118 may be designed and configured to generate further training data and/or to generate outputs using longitudinal data 1120. As used herein, longitudinal data 1120 may include a temporally ordered series of data concerning the same user, or the same cohort of users; for instance, longitudinal data 1120 may describe a series of alimentary instruction sets generated for a user over a period of time such as over the course of a month or year. Longitudinal data 1120 may relate to a series of samples tracking response of one or more elements of dietary data recorded regarding a person undergoing one or more alimentary processes linked to one or more alimentary process labels. Alimentary instruction label learner 118 may track one or more elements of dietary data and fit, for instance, a linear, polynomial, and/or splined function to data points; linear, polynomial, or other regression across larger sets of longitudinal data, using, for instance, any regression process as described above, may be used to determine a best-fit graph or function for the effect of a given alimentary process over time on a dietary request. Functions may be compared to each other to rank alimentary processes; for instance, an alimentary process associated with a steeper slope in curve representing improvement in a dietary request, and/or a shallower slope in a curve representing a slower decline, may be ranked higher than an alimentary process associated with a less steep slope for an improvement curve or a steeper slope for a curve marking a decline. Alimentary processes associated with a curve and/or terminal data point representing a value that does not associate with a previously detected alimentary process label may be ranked higher than one that is not so associated. Information obtained by analysis of longitudinal data 1120 may be added to alimentary process database and/or training set.

With continued reference to FIG. 11, alimentary instruction label learner 118 may utilize past user entries 1124 to continuously update first model 120 and/or second model 128. Past user entries 1124 may include previous dietary requests including for example constitutional restrictions, and user preferences, as well as previous biological extractions. Such information may be continuously supplied to alimentary instruction label leaner 118 to provide real-time data to generate more accurate algorithms and models.

Figure 12:
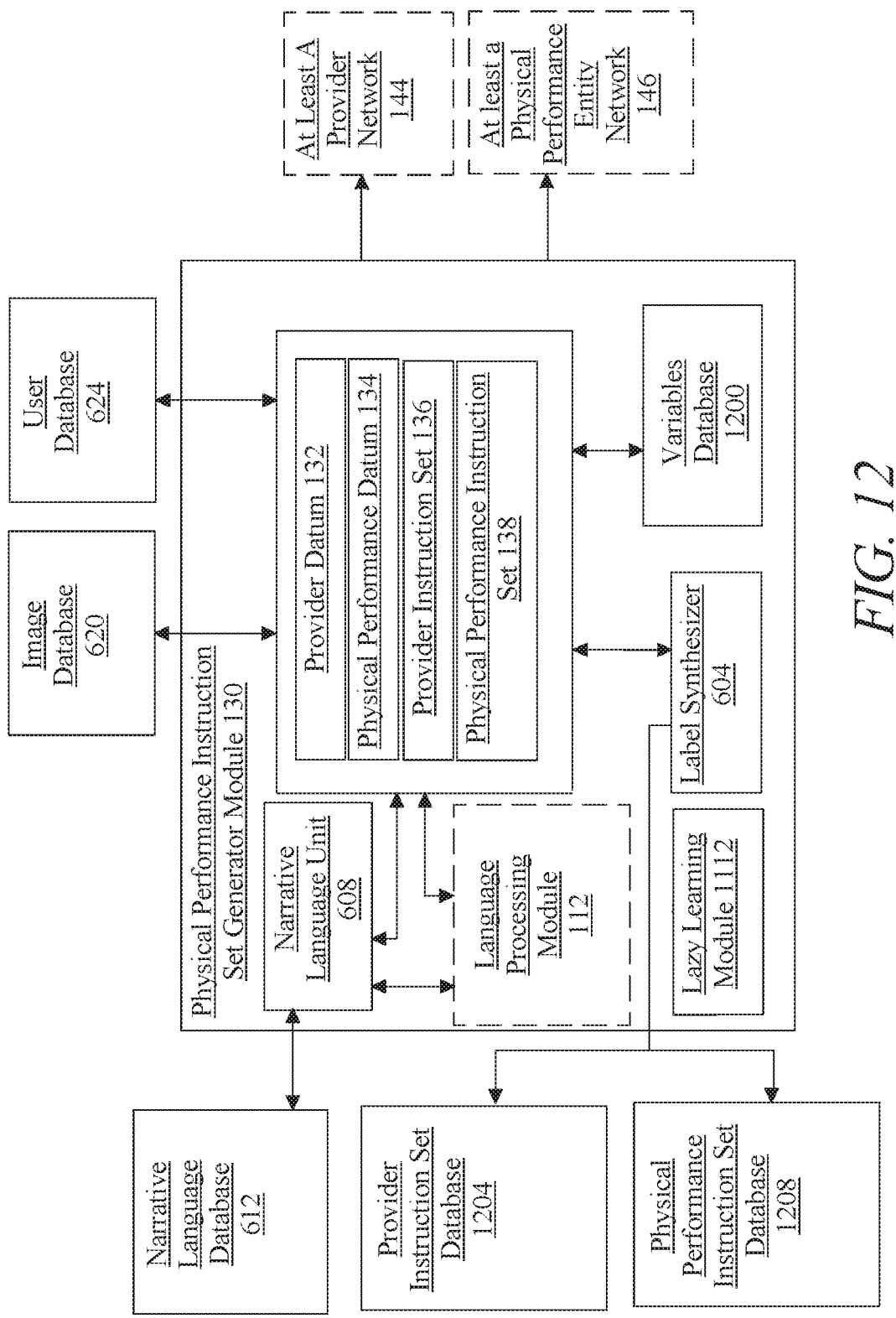
FIG. 12 is a block diagram illustrating an exemplary embodiment of a physical performance instruction set generator module.

Referring now to FIG. 12, an exemplary embodiment of physical performance instruction set generator module 130 is illustrated. Physical performance instruction set generator module 130 may include any hardware or software module as described above. Physical performance instruction set generator module 130 is designed and configured to receive at least a provider datum, receive at least a physical performance datum, select at least a provider and at least a physical performance executor, and generate at least a provider instruction set and at least a physical performance instruction set as a function of the at least a provider datum and the at least a physical performance datum and the at least an alimentary instruction set.

With continued reference to FIG. 12, selecting at least a provider and at least a physical performance executor may be performed by physical performance instruction set generator module 130 by generating a loss function of user specific variables and minimizing the loss function. Physical performance instruction set generator module 130 may utilize variables database 1200 to generate a loss function using different variables and minimize the loss function. Variables that may be utilized and stored within variables database 1200 are described in more detail below in reference to FIG. 13. Loss function may include any of the loss functions as described above in reference to FIG. 1.

With continued reference to FIG. 12, selecting at least a provider and at least a physical performance executor may be performed by physical performance instruction set generator module 130 by utilizing lazy learning methods such as by lazy learning module 1112. Lazy learning methods may include producing a field of the at least a provider and the at least a physical performance executor combination and selecting at the at least a provider and the at least a physical performance executor using a lazy-learning process. Lazy-learning process may include generating algorithms including k-nearest neighbors function. K-nearest neighbors function may include any of the k-nearest neighbors algorithms as described above in reference to FIG. 1. For example, in an embodiment, physical performance instruction set generator module 130 may receive data based on user inputs, provider datums 132, and/or physical performance datums 134 in regards to a dietary request received from a user client device 142. This may include for example, information pertaining to providers and/or physical performance executors who can aid in fulfilling user's dietary request. For example, a provider datums 132 may contain information such as contact information for providers as well as possible menu options for those who can fulfill and prepare food for a user based on user's dietary request. Physical performance datums 134 may contain information such as contact information for physical performance executors who can fulfill and deliver a dietary request for a user. User inputs may include user inputs as to dietary request such as for example user preferences, constitutional restrictions, and user inputs such as preference for a dietary request to arrive at user's residence at a certain time or a request for a certain ingredient or meal for a dietary request. In such an instance, such data and information may be utilized in a k-nearest neighbors function to classify the data points and assign a class label based on distances to known training data vector spaces. Distances may be measured for example using Euclidean distance and other algorithms such as Large Margin Nearest Neighbor and/or neighborhood components analysis. Training data may include a set of data for which class labels are known and used to calculate a value for k, which may be calculated using heuristic techniques such as hyperparameter optimization and bootstrapping methods. K values may then be utilized in addition to weighted contributions of data points that are created from received data including user inputs, provider datums 132, and physical performance datums 134 to calculate and select optimal providers and physical performance executors.

With continued reference to FIG. 12, generation of provider instruction set 136 and/or physical performance instruction set 138 may include identification of one or more provider instruction sets 136 and/or one or more physical performance instruction sets 138 as a function of dietary request and/or alimentary instruction set 116. In an embodiment, generation of provider instruction set 136 and/or physical performance instruction set 138 may include identification of one or more provider instruction sets 136 and/or one or more physical performance instruction sets 138 and insertion of the one or more instruction sets into provider instruction set 136 and/or physical performance instruction set 138. For example, provider instruction set 136 and/or physical performance instruction set 138 may be formed, wholly or partially, by aggregating instruction sets and combining the aggregated instruction sets utilizing narrative language unit 608, narrative language database 612, label synthesizer 604, image database 620, and/or user database 624.

With continued reference to FIG. 12, physical performance instruction set generator module 130 may generate provider instruction set 136 and/or physical performance instruction set 138 by utilizing label synthesizer 604. Label synthesizer 604 may include any of the label synthesizers as described above. Label synthesizer 604 may determine that a first provider instruction set 136 is a duplicate of a second provider instruction set 136 and eliminate the first provider instruction set 136. Determination that a first provider instruction set 136 is a duplicate of a second provider instruction set 136 may be determined for example by consulting language processing module 112 and/or narrative language database 612. In an embodiment, narrative language unit 608, narrative language database 612, and/or language processing module 112 may ensure that information contained within both provider instruction set 136 and/or physical performance instruction set 138 is accurate. For example, provider instruction set 136 and physical performance instruction set 138 may both include contact information for user. In such an instance, language processing module 112 may ensure that contact information is accurate and duplicate of one another so as to ensure that provider instruction set 136 contains accurate contact information for user while physical performance instruction set 138 contains old and outdate contact information for the same user.

With continued reference to FIG. 12, physical performance instruction set generator module 130 may group information contained within provider instruction set 136 and/or physical performance instruction set 138 according to one or more classification systems relating categories of information. For example, physical performance instruction set generator module 130 may group information into categories such as information that will be contained exclusively within provider instruction set 136, information that will be contained exclusively within physical performance instruction set 138, and information that will be shared will be shared and contained within provider instruction set 136 and physical performance instruction set 138.

With continued reference to FIG. 12, physical performance instruction set generator module 130 may be configured to generate provider instruction set 136 and/or physical performance instruction set 138 by converting one or more alimentary instruction sets 116 into narrative language. For example, physical performance instruction set generator module 130 may include and/or communicate with narrative language unit 608, which may be configured to determine an element of narrative language associated with at least an alimentary instruction set and include the element of narrative language in provider instruction set 136 and/or physical performance instruction set 138. Narrative language unit 608 may implement this, without limitation, by using language processing module 112 to detect one or more associations between alimentary instruction set labels, or lists of alimentary instruction set labels, and phrases and/or statements of narrative language. Alternatively or additionally, narrative language unit 608 may retrieve one or more elements of narrative language from narrative language database 612, which may contain one or more tables associating alimentary instruction set labels and/or groups of alimentary instruction set labels with words, sentences, and/or phrases of narrative language. One or more elements of narrative language may be included in alimentary instruction set, for instance for display to a user as text describing a current alimentary instruction set status of the user.

Figure 14:
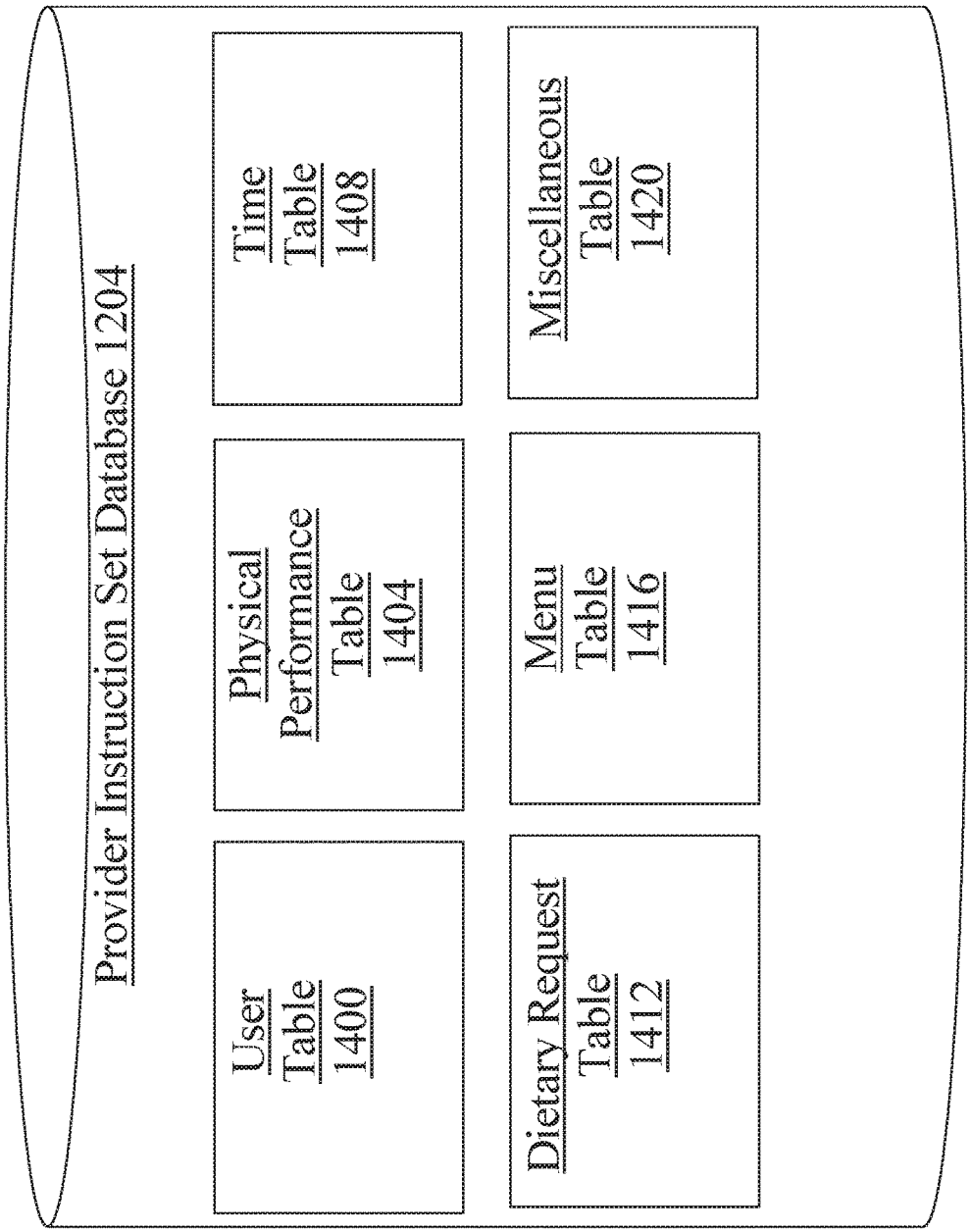
FIG. 14 is a block diagram illustrating an exemplary embodiment of a provider instruction set database.
Figure 15:
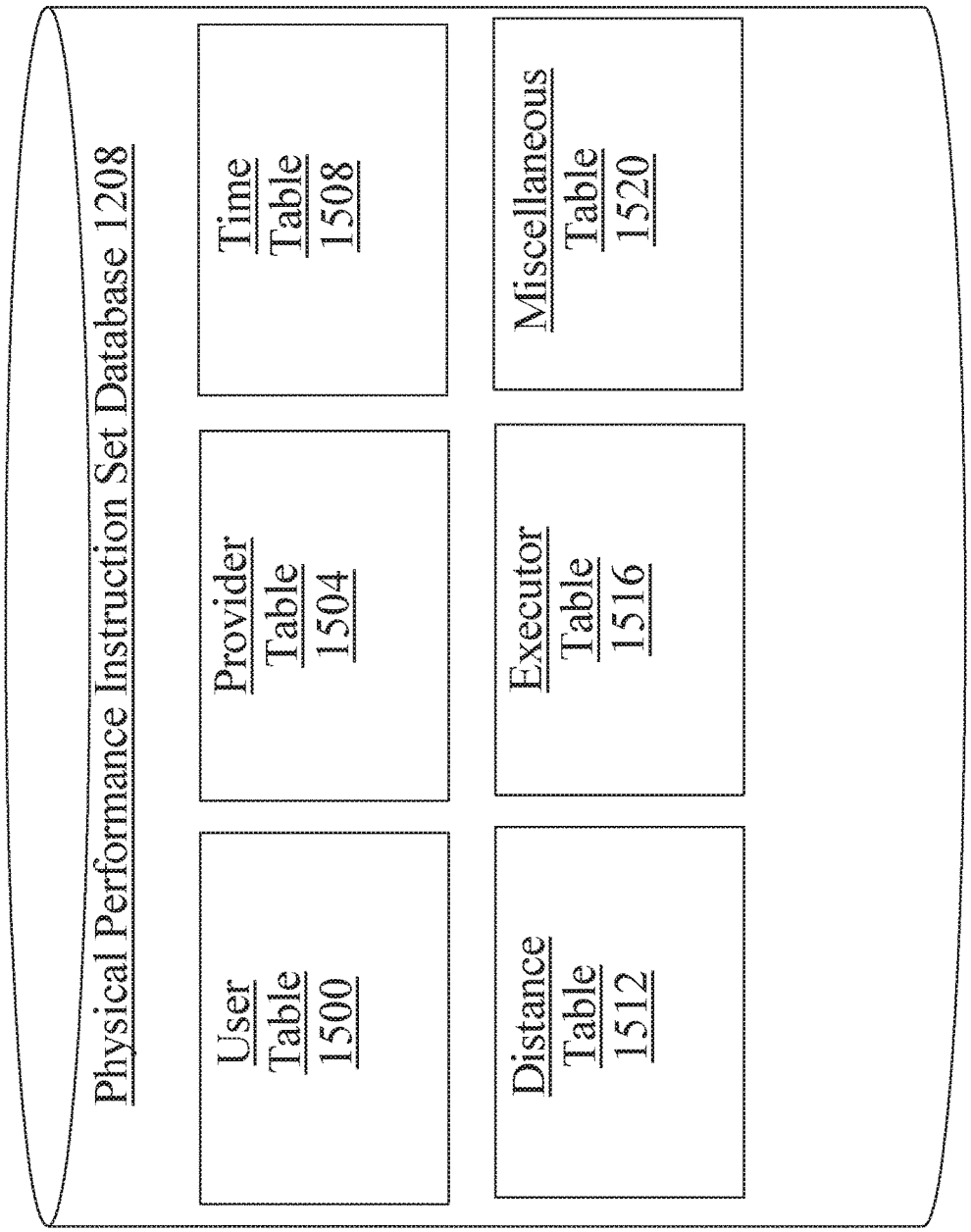
FIG. 15 is a block diagram illustrating an exemplary embodiment a physical performance instruction set database.

With continued reference to FIG. 12, relationships between alimentary instruction sets, provider instruction sets, and/or physical performance instruction sets may be retrieved from provider instruction database 1204, and/or physical performance instruction database 1208, for instance by generating a query using one or more inputs, entering the query, and receiving one or more categories matching the query from provider instruction database 1204 and/or physical performance instruction database 1208 as described in more detail below in reference to FIGS. 14-15.

With continued reference to FIG. 12, physical performance instruction set generator module 130 may receive provider datums from provider network 144. Provider network 144 may include any of the provider networks as described above in reference to FIG. 1. Physical performance instruction set generator module 130 may receive physical performance datums 134 from physical performance entity network 146. Physical performance entity network 146 may include any of the physical performance entity networks 146 as described above in reference to FIG. 1.

Figure 13:
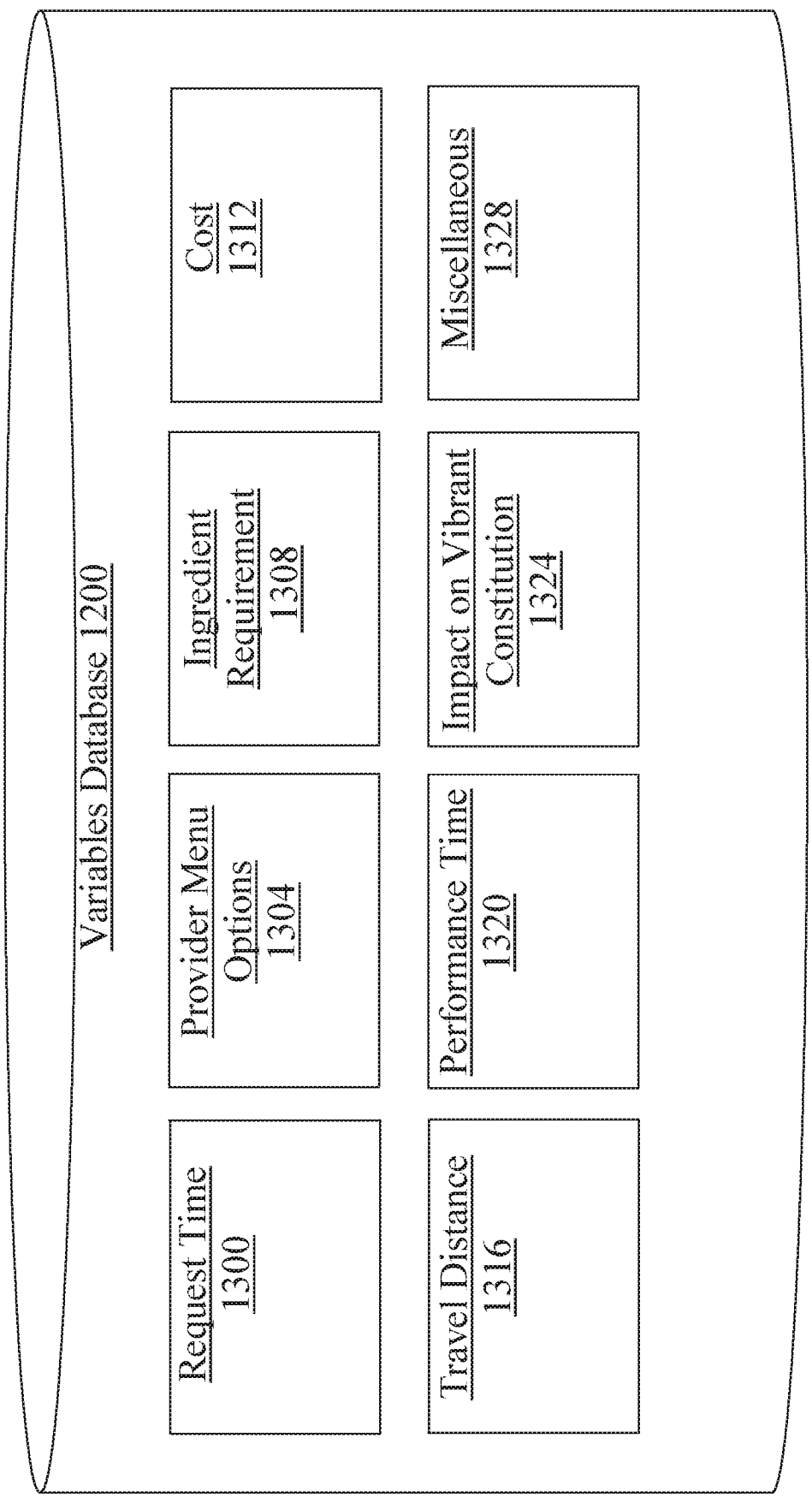
FIG. 13 is a block diagram illustrating an exemplary embodiment of a variables database.

Referring now to FIG. 13, an exemplary embodiment of variables database 1200 is illustrated. Variables database 1200 may be implemented as any database and/or datastore suitable for use as dietary database 200 as described above. One or more database tables in variables database 1200 may include, without limitation request time 1300; request timetable 1300 may include information pertaining to how far in advance a user may be requesting a dietary input. For example, a user may generate a dietary request once weekly on Sunday nights to receive a dietary request with a week's worth of meals every Wednesday. In yet another non-limiting example, a user may generate a dietary request to receive a dietary request in a shorter amount of time such as within a few mere hours minutes. One or more database tables in variables database 1200 may include, without limitation provider menu options 1304; provider menu options 1304 may include information pertaining to what types of meals and selects a user prefers from a certain provider. For example, a user may habitually order spaghetti Bolognese from a certain provider and ginger salmon with vegetables form another provider. One or more database tables in variables database 1200 may include, without limitation ingredient requirement table 1308; ingredient requirement table 1308 may include information pertaining to certain ingredients may require to include in a dietary request and/or require to eliminate in a dietary request. Ingredient requirement may include for example certain ingredients a user may require to include in a dietary request such as a requirement for a certain food group such as protein or carbohydrates, or a requirement for a certain ingredient such as avocado or wild tuna. Ingredient requirement may include for example certain ingredients a user may require to eliminate such as because of a user preference or constitutional restriction. For example, a user with a tree nut allergy may require elimination of all tree nuts and tree nut containing food items. In yet another non-limiting example, a user may report an ingredient requirement that includes a preference to eliminate any egg containing products because of an aversion to eggs. A user may report an ingredient requirement such as a requirement to eliminate all gluten containing foods and gluten containing food products because of a self-reported gluten intolerance. A user may report an ingredient requirement such as a preference for all organic ingredients, all locally sourced ingredients, all non-genetically modified ingredients and the like. One or more database tables in variables database 1200 may include, without limitation cost table 1312; cost table may include information pertaining to cost a user is willing to spend on a dietary request. Cost table may include information such as how much money a user is willing to spend on a particular meal, a particular number of meals, a week's worth of meals, and the like. For example, a user may have a total budget for a week's worth of meals that may include a breakdown by how much a user wishes to spend on a week's worth of breakfast, how much a user wishes to spend on a week's worth of lunch, and how much a user wishes to spend on a week's worth of dinner. One or more database tables in variables database 1200 may include, without limitation travel time table 1316; travel distance table 1316 may include information pertaining to a limit on travel distance for any one particular performance provider executor. For example, a user who will be receiving a meal that has been freshly prepared and served hot may prefer a performance provider executor with a shorter travel distance than a user who will be receiving a week's worth of frozen meals. One or more database tables in variables database 1200 may include, without limitation performance time table 1320; performance time table 1320 may include information pertaining time requests generated by a user in regards to physical performance executor. For example, a user may prefer a physical performance executor who can deliver a dietary request within ten minutes from a provider while another user may prefer a physical performance executor who can deliver a dietary request within three days. One or more database tables in variables database 1200 may include, without limitation impact on vibrant constitution table 1324; impact on vibrant constitution table 1324 may include information pertaining to a user's particular long term health goals which may be contain dietary restraints and restrictions and current health state. For example, a user with a recent c-difficile infection and currently taking an antibiotic such as metronidazole may have information contained within impact on vibrant constitution table 1324 containing dietary restraints while on metronidazole that include zero consumption of alcohol. In yet another non-limiting example, a user with long term health goal to lose body fat and increase muscle mass may have information contained within impact on vibrant constitution table 1324 containing dietary restraints generated by user such as a reduction in carbohydrates and an increased consumption of protein. One or more database tables in variables database 1200 may include, without limitation miscellaneous table 1328; miscellaneous table 1328 may include miscellaneous information that may be utilized in selecting at least a physical performance executor and/or generating at least a physical performance instruction set. For example, a female user who lives alone may prefer a physical performance executor who is female or a user with an anaphylactic reaction to shell-fish may prefer a provider who has a certain level of training or experience in food preparation for individuals with anaphylactic reactions.

Referring now to FIG. 14, an exemplary embodiment of provider instruction set database 1204 is illustrated. Provider instruction set database 1204 may be implemented as any database and/or datastore suitable for use as dietary database 200 as described above. Provider instruction set database may be configured to be utilized by physical performance instruction set generator module 130 to generate provider instruction set 136. Alternatively or additionally, provider instruction set database 1204 may retrieve one or more elements from any database within system 100. One or more tables in provider instruction set database 1204 may include, without limitation, user table 1400; user table 1400 may include information pertaining to a particular user. This may include for example, user contact information, user preferences for specific providers, previous interactions of a user with a particular provider, stored payment information, and user's dietary preferences. One or more tables in provide instruction set database 1204 may include, without limitation, physical performance table 1404; physical performance table 1404 may include information pertaining to a particular physical performance entity and/or physical performance executor. This may include for example, physical performance entity and/or physical performance executor contact information, mode of transportation, credentials and the like. One or more tables in provider instruction set database 1204 may include, without limitation, time table 1408; time table 1408 may include information such as time for a provider to prepare a dietary request, hours of operation of a provider, and the like. One or more tables in provider instruction set database 1204 may include, without limitation dietary request table 1412; dietary request table 1412 may include information pertaining to particular dietary requests and a provider's ability to accommodate such a request. For example, dietary request table 1412 may include a list of dietary requests that a particular provider may prepare meals for such as gluten free, dairy free, soy free, ketogenic, paleo, Atkins, raw foods, vegan, vegetarian, macrobiotic, and the like. One or more tables in provider instruction set database 1204 may include, without limitation menu table 1416; menu table 1416 may include information pertaining to particular menu items a provider may prepare at any one time such as a weekly menu, daily menu, seasonal menu, menu by meal, and the like. For example, menu table 1416 may include information such as a provider's selection of three dinner choices on any one given night. One or more tables in provider instruction set database 1204 may include, without limitation miscellaneous table 1420; miscellaneous information may include any other information that may be useful in selecting a provider and/or generating at least a provider instruction set.

Referring now to FIG. 15, an exemplary embodiment of physical performance instruction set database 1208 is illustrated. Physical performance instruction set database 1208 may be implemented as any database and/or datastore suitable for use as dietary database 200 as described above. Physical performance instruction set database 1208 may be configured to be utilized by physical performance instruction set generator module 130 to generate physical performance instruction set 138. Alternatively or additionally, physical performance instruction set database 1208 may retrieve one or more elements from any database within system 100. One or more tables in physical performance instruction set database 1208 may include, without limitation, user table 1500; user table 1500 may include information pertaining to a particular user. This may include for example, user contact information, user preferences for delivery within a specific amount of time, previous interactions of a user with a physical performance executor, stored payment information, user preferences such as location of delivery or directions as to where a dietary request should be left at user's residence office location. One or more tables in physical performance instruction set database 1208 may include provider table 1504; provider table 1504 may include information pertaining to a particular provider. This may include for example, provider contact information, provider instructions for physical performance executor upon arrival at provider's location, storage and handling information pertaining to a dietary request during transport, previous interactions with provider, and the like. One or more tables in physical performance instruction set database 1208 may include, without limitation, time table 1508; time table 1508 may include time of operation of a particular physical performance entity and/or physical performance executor. For example, time table 1508 may include particular times of operation of a physical performance executor. One or more tables in physical performance instruction set database 1208 may include, without limitation, distance table 1512; distance table 1512 may include information pertaining to how far a distance a particular physical performance executor may be willing to travel. Distance may include a certain mileage distance for any one particular delivery, a certain geographical distance for any one particular delivery, a certain mileage distance for any one particular shift of work, a certain geographical distance for any one particular shift, and/or any other distance over a certain period of time. For example, a physical performance executor who works in New England may have a preference to deliver dietary requests within a one hundred mile radius of Nashua, New Hampshire. In yet another non limiting example, a physical performance executor who resides in California may have a preference to deliver dietary requests within a thirty mile radius of executor's house because of heavy traffic and congestion on the roads. One or more tables in physical performance instruction set database 1208 may include executor table 1516; executor table 1516 may include information pertaining to any one particular executor including executor contact details, executor identification, executor mode of transportation, executor make and model of executor mode of transportation, and the like. For example, executor table 1516 may include details about an executor's car such as license plate, car color, and car model. In yet another non-limiting example, executor table 1516 may include a particular executor's credentials such as a captain's boating license or a train conductor's license and experience. One or more tables in physical performance instruction set database 1208 may include miscellaneous table 1520; miscellaneous table 1520 may include any other information that may be pertinent in regards to generating physical performance instruction set. Miscellaneous table 1520 may include information such as cost associated with different modes of transportation such as the price for a scoter delivery versus the cost for an airplane delivery.

Figure 16:
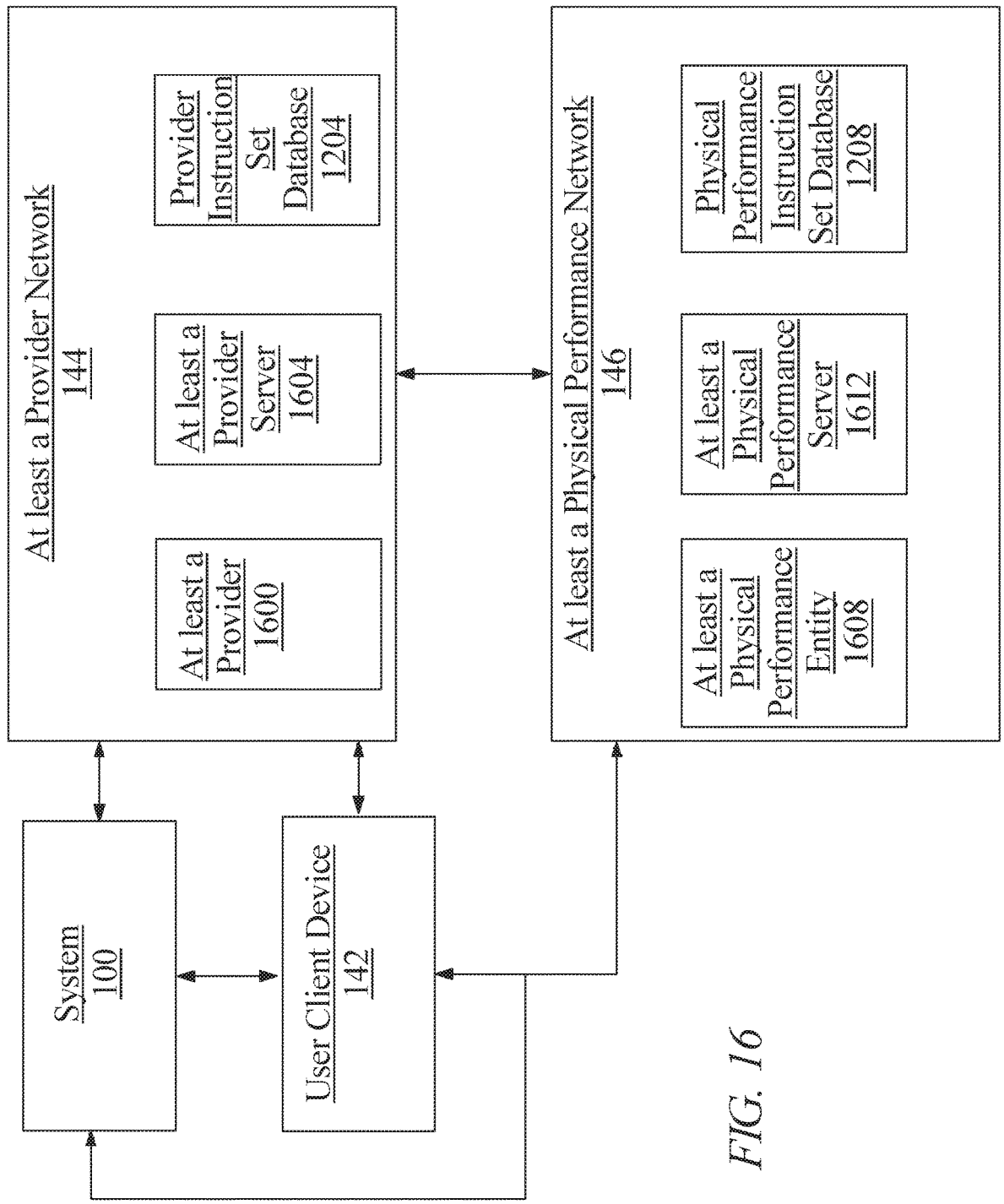
FIG. 16 is a block diagram illustrating an exemplary embodiment of a provider network and a physical performance network.

Referring now to FIG. 16, an exemplary embodiment of at least a provider network 144 and at least a physical performance network 144 is illustrated. In an embodiment, at least a provider network 144 may include at least a provider 1600. At least a provider 1600 may include any of the providers as described above. At least a provider 1600 may execute a provider performance. At least a provider network 144 may include at least a provider server 1604. At least a provider server 1604 may include any computing device suitable for use as the at least a server 102. At least a provider network 144 may include provide instruction set database 1204. Provider instruction set database 1204 may include any of the database structures as described above in reference to FIG. 12, and FIG. 14. At least a provider network 144 may transit and receive information from system 100, user client device 142, and/or at least a physical performance network 144. This may be done using any transmission methodologies including for example network transmission as described herein. In an embodiment, system 100, user client device 142, and/or at least a physical performance network 146 may be designed and configured to interact with a plurality of provider networks 144.

With continued reference to FIG. 16, at least a physical performance network 146 may include at least a physical performance entity 1608. At least a physical performance network 146 may include at least a physical performance server 1612. At least a physical performance server 1612 may include any computing device suitable for use as the at least a server 102. At least a physical performance network 146 may include at least a physical performance instruction set database 1208. At least a physical performance instruction set database 1208 may include any of the database structures as described above in reference to FIG. 12, and FIG. 15. At least a physical performance network 146 may transmit and receive information from system 100, user client device 142, and/or at least a provider network 144. This may be done using any transmission methodologies including for example any network transmission as described herein. In an embodiment, system 100, user client device 142, and/or at least a provider network 144 may be designed and configured to interact with a plurality of physical performance networks 146.

Figure 17:
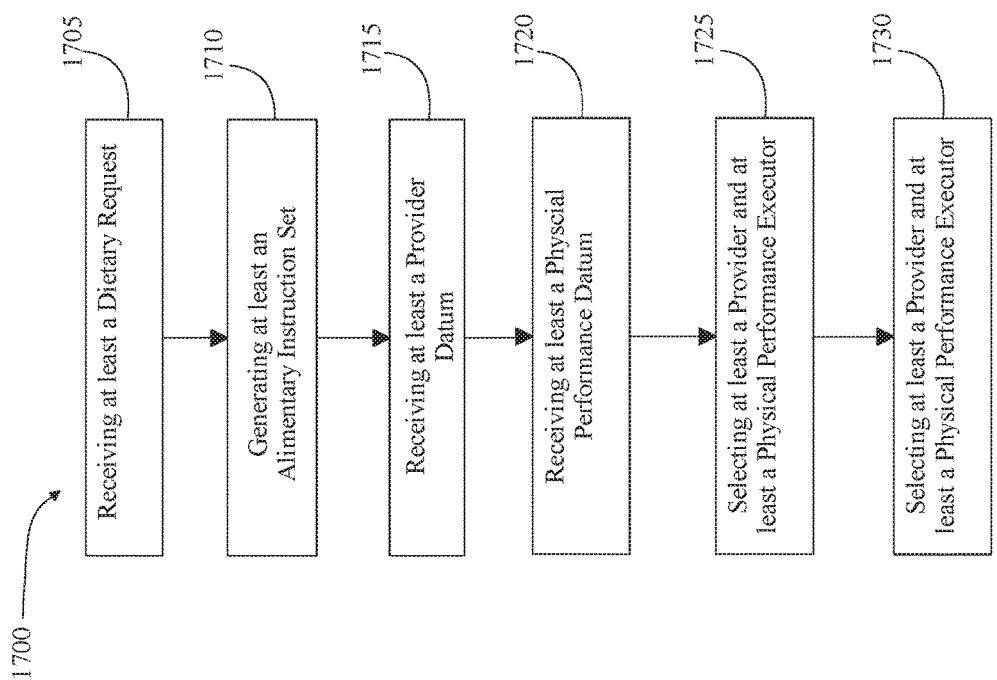
FIG. 17 is a flow diagram illustrating an exemplary embodiment of a method of optimizing dietary levels.

Referring now to FIG. 17, an exemplary embodiment of a method 1700 of optimizing dietary levels utilizing artificial intelligence is illustrated. At step 1705 at least a server receives at least a dietary request from a user client device. The at least a server may include any of the servers as described herein. The at least a dietary request may include any of the dietary requests as described above in reference to FIGS. 1-17. At least a dietary request may include a request for a particular diet, food, ingredient, food group, nutrition plan, style of eating, lifestyle, and/or nutrition. At least a dietary request may include a request for a particular meal, and/or a particular number of meals such as a week's worth of lunches or a week's worth of breakfast, lunch, and dinner. Receiving at least a dietary request may include receiving at least a biological extraction from a user. At least a biological extraction may include any of the biological extractions as described above in reference to FIGS. 1-17. Receiving at least a dietary request from a user client device may include receiving at least a datum of user data including a user preference. A user preference may include any of the user preferences as described above in reference to FIGS. 1-17. A user preference may include a preference for a certain style of eating such as a user's preference to consume a paleo diet for personal weight loss goals or a user preference for a vegetarian diet for ethical reasons. Receiving at least a dietary request from a user client device may include receiving a constitutional restriction. A constitutional restriction may include any of the constitutional restrictions as described above in reference to FIGS. 1-17. A constitutional restriction may include a user's self-reported intolerance to a certain food or food group, such as for example a user's self-reported lactose intolerance due to cramping and upset stomach upon consuming excess amounts of dairy products. A constitutional restriction may include a user's self-reported allergy to a food or food group as previously diagnosed by a medical professional such as a functional medical doctor. For example, a user with a previously diagnosed allergy to tree nuts may self-report a constitutional restriction to avoid all tree nuts and tree nut containing ingredients.

With continued reference to FIG. 17, at step 1710 the at least a server generates at least an alimentary instruction set as a function of the at least a dietary request. Alimentary instruction set may include any of the alimentary instruction sets as described above in reference to FIGS. 1-17. Generating the at least an alimentary instruction set may be done utilizing any of the methodologies as described above in reference to FIGS. 1-17. In an embodiment, the at least an alimentary instruction set may be generated utilizing training data. The at least a server may be configured to receive training data wherein receiving the training data includes receiving a first training set including a plurality of first data entries, each first data entry of the plurality of first data entries including at least an element of dietary request data and at least a correlated alimentary process label. In an embodiment, the at least a server may utilize training data and the at least a dietary request to generate at least a correlated alimentary process label utilizing any of the methodologies as described above in reference to FIGS. 1-17.

With continued reference to FIG. 17, the at least a server may receive at least a biological extraction from a user and generate the at least an alimentary instruction set as a function of the at least a biological extraction. Biological extraction may include any of the biological extractions as described above in reference to FIGS. 1-17. Generating the at least an alimentary instruction set as a function of the at least a biological extraction may include receiving a second training set including a plurality of second data entries, each second data entry of the plurality of second data entries including at least an element of biological extraction data and at least a correlated alimentary process label and generating the at least an alimentary instruction set as a function of the at least a biological extraction and the training data.

With continued reference to FIG. 17, at step 1715 the at least a server receives at least a provider datum. At least a provider datum may include any of the provider datums as described above in reference to FIGS. 1-17. At least a provider datum may include any element of data describing the provider, the provider's ability to prepare food for a certain dietary request, the provider's preference to prepare food within a certain geographical location, and/or a menu selection of food options that a provider may be able to prepare such as a weekly menu of food options. A provider datum may include for example, a provider's menu choices for a user that may be adherent to certain diets such as a menu containing meal options that include meals that may be made gluten free, dairy free, ketogenic, vegan, and low carbohydrate for example.

With continued reference to FIG. 17, at step 1720 the at least a server receives at least a physical performance datum. At least a physical performance datum may include any of the physical performance datums as described above in reference to FIGS. 1-17. The at least a physical performance datum may include for example any element of data describing the physical performance executor, the physical performance executor's ability to deliver a dietary request such as a meal based on certain constraints such as a physical performance executor's ability to deliver a dietary request such as a meal within a certain amount of time, the physical performance executor's ability to pick up a dietary request such as a meal from a provider within a certain geographical location, the physical performance executor's ability to deliver a dietary request such as a meal to a user located within a certain geographical location and the like. The at least a physical performance datum may include for example a physical performance executor's ability to deliver a dietary request within a certain geographical area or within a certain period of time.

With continued reference to FIG. 17, at step 1725 the at least a server selects at least a provider and at least a physical performance executor. Selecting the at least a provider and the at least a physical performance executor may be performed using any of the methodologies as described above in reference to FIGS. 1-17. Selecting the at least a provider and the at least a physical performance executor may include generating a los function of user specific variables and minimizing the loss function. Loss function may include any of the loss functions as described above in reference to FIGS. 1-17. User specific variables may include any of the user specific variables as described above in reference to FIG. 12 and FIG. 13. User specific variables may be customized around user specific inputs and selections. Selecting the at least a provider and the at least a physical performance executor may include producing a field of combinations of the at least a provider and the at least a physical performance executor and selecting the at least a provider and the at least a physical performance executor using a lazy-learning learning process. Lazy-learning process may include any of the lazy learning processes as described above in reference to FIGS. 1-17. Lazy-learning process may include for example generating a k-nearest neighbors function. K-nearest neighbors function may include any of the k-nearest neighbors function as described above in reference to FIGS. 1-17.

With continued reference to FIG. 17, at step 1730 the at least a server generates at least a provider instruction set and at least a physical performance instruction set as a function of the at least a provider datum and the at least a physical performance datum and the at least an alimentary instruction set. Generating the at least a provider instruction set and generating the at least a physical performance datum may be done utilizing any of the methodologies as described above in reference to FIGS. 1-17. Generating the at least a provider instruction set and generating the at least a physical performance datum may include receiving at least a user input datum. User input datum may include any of the user input datums as described above in reference to FIGS. 1-17. In an embodiment, the at least a user input datum may include at least a user constraint. At least a user constraint may include any of the user constraints as described above in reference to FIGS. 1-17. Generating the at least a provider instruction set and the at least a physical performance instruction set may include receiving at least a user constraint, selecting at least a provider and at least a physical performance executor as a function of the at least constraint and transmitting a subset of data associated with the at least a user to the at least a provider and the at least a physical performance executor. Selecting at least a provider and at least a physical performance executor may include selecting as a function of fulfilling the constraint. For example, at least a provider and/or at least a physical performance executor who can fulfill the user constraint may be selected while at least a provider and/or at least a physical performance executor who cannot fulfill the user constraint may not be selected. In an embodiment, transmitting a subset of data associated with the user may occur using any of the transmission methodologies as described herein.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 18:
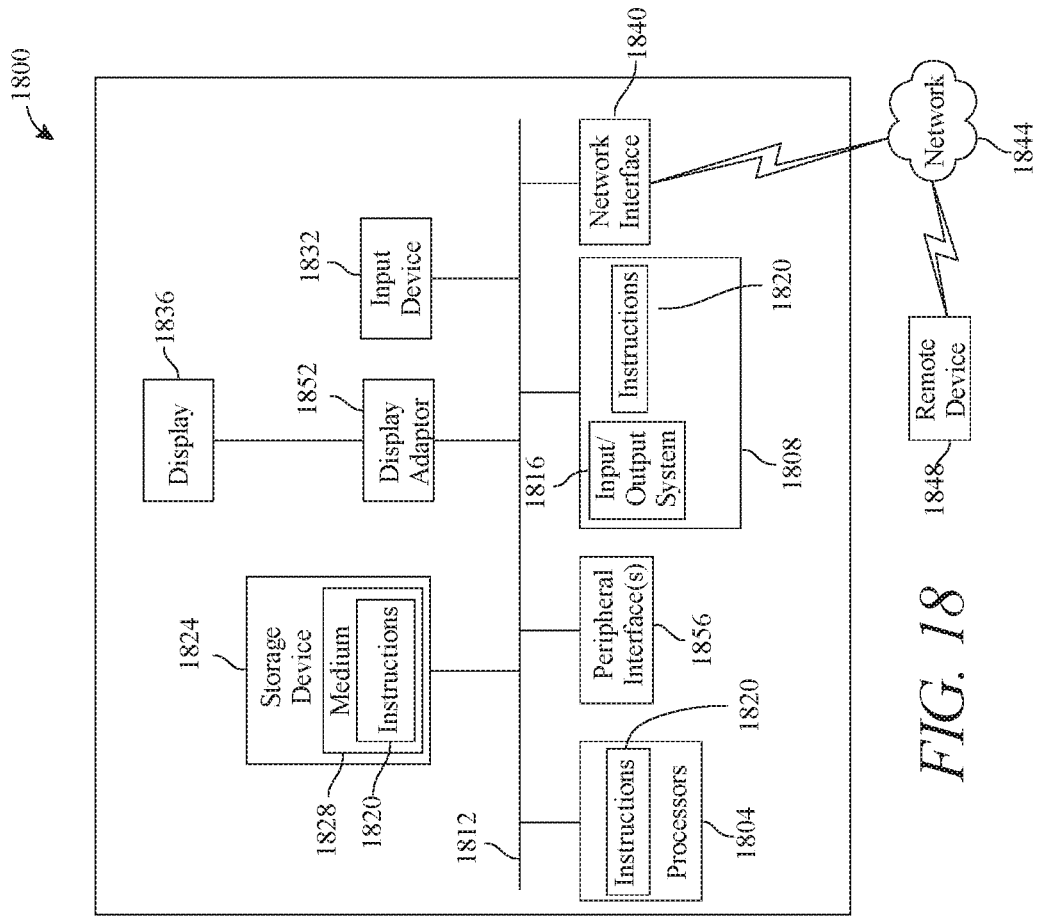
FIG. 18 is a block diagram of a computing system that can be used to implement any one or more of the methodologies disclosed herein and any one or more portions thereof.

FIG. 18 shows a diagrammatic representation of one embodiment of a computing device in the exemplary form of a computer system 1800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1800 includes a processor 1804 and a memory 1808 that communicate with each other, and with other components, via a bus 1812. Bus 1812 may include any of several types of bus structures including, but not limited to, a memory bus, a memory controller, a peripheral bus, a local bus, and any combinations thereof, using any of a variety of bus architectures.

Memory 1808 may include various components (e.g., machine-readable media) including, but not limited to, a random access memory component, a read only component, and any combinations thereof. In one example, a basic input/output system 1816 (BIOS), including basic routines that help to transfer information between elements within computer system 1800, such as during start-up, may be stored in memory 1808. Memory 1808 may also include (e.g., stored on one or more machine-readable media) instructions (e.g., software) 1820 embodying any one or more of the aspects and/or methodologies of the present disclosure. In another example, memory 1808 may further include any number of program modules including, but not limited to, an operating system, one or more application programs, other program modules, program data, and any combinations thereof.

Computer system 1800 may also include a storage device 1824. Examples of a storage device (e.g., storage device 1824) include, but are not limited to, a hard disk drive, a magnetic disk drive, an optical disc drive in combination with an optical medium, a solid-state memory device, and any combinations thereof. Storage device 1824 may be connected to bus 1812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1824 (or one or more components thereof) may be removably interfaced with computer system 1800 (e.g., via an external port connector (not shown)). Particularly, storage device 1824 and an associated machine-readable medium 1828 may provide nonvolatile and/or volatile storage of machine-readable instructions, data structures, program modules, and/or other data for computer system 1800. In one example, software 1820 may reside, completely or partially, within machine-readable medium 1828. In another example, software 1820 may reside, completely or partially, within processor 1804.

Computer system 1800 may also include an input device 1832. In one example, a user of computer system 1800 may enter commands and/or other information into computer system 1800 via input device 1832. Examples of an input device 1832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1832 may be interfaced to bus 1812 via any of a variety of interfaces (not shown) including, but not limited to, a serial interface, a parallel interface, a game port, a USB interface, a FIREWIRE interface, a direct interface to bus 1812, and any combinations thereof. Input device 1832 may include a touch screen interface that may be a part of or separate from display 1836, discussed further below. Input device 1832 may be utilized as a user selection device for selecting one or more graphical representations in a graphical interface as described above.

A user may also input commands and/or other information to computer system 1800 via storage device 1824 (e.g., a removable disk drive, a flash drive, etc.) and/or network interface device 1840. A network interface device, such as network interface device 1840, may be utilized for connecting computer system 1800 to one or more of a variety of networks, such as network 1844, and one or more remote devices 1848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1844, may employ a wired and/or a wireless mode of communication. In general, any network topology may be used. Information (e.g., data, software 1820, etc.) may be communicated to and/or from computer system 1800 via network interface device 1840.

Computer system 1800 may further include a video display adapter 1852 for communicating a displayable image to a display device, such as display device 1836. Examples of a display device include, but are not limited to, a liquid crystal display (LCD), a cathode ray tube (CRT), a plasma display, a light emitting diode (LED) display, and any combinations thereof. Display adapter 1852 and display device 1836 may be utilized in combination with processor 1804 to provide graphical representations of aspects of the present disclosure. In addition to a display device, computer system 1800 may include one or more other peripheral output devices including, but not limited to, an audio speaker, a printer, and any combinations thereof. Such peripheral output devices may be connected to bus 1812 via a peripheral interface 1856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for optimizing dietary levels utilizing artificial intelligence, the system comprising:
    at least a server, the at least a server is designed and configured to:
        receive training data, wherein the training data includes a plurality of data entries, each data entry of the plurality of data entries including at least a dietary request and at least a correlated alimentary process label; and
        receive at least a dietary request and at least a user input from a user client device associated with a user;
    an alimentary instruction set generator module operating on the at least a server, the alimentary instruction set generator module designed and configured to:
        input the training data to a machine learning algorithm;
        train a machine learning model as a function of the machine learning algorithm and the training data;
        generate, via the machine learning model, at least an alimentary instruction set as a function of the at least a dietary request received from the user client device and the training data, wherein the at least an alimentary instruction set identifies a meal to be delivered to the user;
    a physical performance instruction set generator module operating on the at least a server, the physical performance instruction set generator module designed and configured to:
        receive at least a provider datum for each provider of a plurality of providers;
        receive at least a physical performance datum;
        select at least a provider and at least a physical performance executor as a function of the alimentary instruction set and the at least a user input, wherein selecting the at least a provider further comprises:
            generating at least a mathematical expression representing a variable output, wherein the at least a mathematical expression comprises the at least a provider datum, the at least a user input, and at least an element of the alimentary instruction set;
            optimizing the variable output; and
            classifying the at least a provider as a function of the optimized variable output;
        wherein the selected at least a provider is configured to prepare the identified meal and the at least a physical performance executor includes a transportation channel configured to deliver the prepared meal to the user; and
        generate at least a provider instruction set and the at least a physical performance instruction set as a function of the at least a provider datum and the at least a physical performance datum and the at least an alimentary instruction set, wherein the provider instruction set includes requirements for a delivery of the meal from the at least a provider to the at least a physical performance executor and requirements for a delivery of the meal from the at least a physical performance executor to the user.

2. The system of claim 1, wherein receiving the at least a dietary request from a user client device further comprises receiving at least a datum of user data including a user preference.

3. The system of claim 1, wherein receiving the at least a dietary request from a user client device further comprises receiving a constitutional restriction.

4. The system of claim 1, wherein:
the at least a server is further configured to receive the at least a dietary request from a user device by receiving at least a biological extraction from a user; and
the alimentary instruction set generator module is further configured to generate the at least an alimentary instruction set as a function of the at least a biological extraction.

5. The system of claim 4, wherein:
the at least a server is further configured to receive a second training set including a plurality of second data entries, each second data entry of the plurality of second data entries including at least an element of biological extraction data and at least a correlated alimentary process label; and
the alimentary instruction set generator module is further configured to generate the at least an alimentary instruction set as a function of the at least a biological extraction and the second training set.

6. The system of claim 1, wherein selecting the at least a provider and the at least a physical performance executor further comprises:
generating a loss function of user specific variables; and
minimizing the loss function.

7. The system of claim 1, wherein selecting the at least a provider and the at least a physical performance executor further comprises:
producing a field of combinations of the at least a provider and the at least a physical performance executor; and
selecting the at least a provider and the at least a physical performance executor using a lazy-learning process.

8. The system of claim 1, wherein generating the at least a provider instruction set and the at least a physical performance instruction set further comprises receiving at least a user input datum including at least a user constraint.

9. The system of claim 8, wherein generating the at least a provider instruction set and the at least a physical performance instruction set further comprises:
selecting at least a provider and at least a physical performance executor as a function of the at least a constraint; and
transmitting a subset of data associated with the at least a user to the at least a provider and the at least a physical performance executor.

10. A method of optimizing dietary levels utilizing artificial intelligence the method comprising:
receiving training data, wherein the training data includes a plurality of data entries, each data entry of the plurality of data entries including at least a dietary request and at least a correlated alimentary process label;
receiving at least a dietary request and at least a user input from a user client device associated with a user;
inputting the training data to a machine learning algorithm;
training a machine learning model as a function of the machine learning algorithm and the training data;
generating, via the machine learning model, at least an alimentary instruction set as a function of the at least a dietary request received from the user client device and the training data, wherein the at least an alimentary instruction set identifies a meal to be delivered to the user
relating the dietary restriction to a user propensity for a second dietary restriction; and
determining the meal to be delivered as a function of the relationship between the dietary restriction and the user propensity for the second dietary restriction;
receiving at least a provider datum for each provider of a plurality of providers;
receiving at least a physical performance datum;
selecting at least a provider and at least a physical performance executor as a function of the alimentary instruction set and the at least a user input, wherein selecting the at least a provider further comprises:
generating at least a mathematical expression representing a variable output, wherein the at least a mathematic expression comprises the at least a provider datum, the at least a user input, and at least an element of the alimentary instruction set;
optimizing the variable output; and
selecting the at least a provider as a function of the optimized variable output;
wherein the selected at least a provider is configured to prepare the identified meal and the at least a physical performance executor includes a transportation channel configured to deliver the prepared meal to the user; and
generating at least a provider instruction set and the at least a physical performance instruction set as a function of the at least a provider datum and the at least a physical performance datum and the at least an alimentary instruction set, wherein the provider instruction set includes requirements for a delivery of the meal from the at least a provider to the at least a physical performance executor and requirements for a delivery of the meal from the at least a physical performance executor to the user.

11. The method of claim 10, wherein receiving the at least a dietary request from a user client device further comprises receiving at least a datum of user data including a user preference.

12. The method of claim 10, wherein receiving the at least a dietary request from a user client device further comprises receiving a constitutional restriction.

13. The method of claim 10, wherein receiving the at least a dietary request and generating the at least an alimentary instruction set further comprises:
receiving at least a biological extraction from a user; and
generating the at least an alimentary instruction set as a function of the at least a biological extraction.

14. The method of claim 13, wherein generating the at least an alimentary instruction set further comprises:
receiving a second training set including a plurality of second data entries, each second data entry of the plurality of second data entries including at least an element of biological extraction data and at least a correlated alimentary process label; and
generating the at least an alimentary instruction set as a function of the at least a biological extraction and the second training set.

15. The method of claim 10, wherein selecting the at least a provider and the at least a physical performance executor further comprises:
generating a loss function of user specific variables; and
minimizing the loss function.

16. The method of claim 10, wherein selecting the at least a provider and the at least a physical performance executor further comprises:
producing a field of combinations of the at least a provider and the at least a physical performance executor; and
selecting the at least a provider and the at least a physical performance executor using a lazy-learning process.

17. The method of claim 10, wherein generating the at least a provider instruction set and the at least a physical performance instruction set further comprises receiving at least a user input datum including at least a user constraint.

18. The method of claim 17, wherein generating the at least a provider instruction set and the at least a physical performance instruction set further comprises:
   selecting at least a provider and at least a physical performance executor as a function of the at least a constraint; and
   transmitting a subset of data associated with the at least a user to the at least a provider and the at least a physical performance executor.

19. The system of claim 1, wherein the machine-learning algorithm comprises a supervised machine-learning process and the mathematical expression comprises an unsupervised machine-learning process.

20. The system of claim 1, wherein the machine-learning algorithm comprises a supervised machine-learning process and the mathematical expression comprises an unsupervised machine-learning process.

\* \* \* \* \*